US012419689B2

(12) United States Patent
Camino et al.

(10) Patent No.: US 12,419,689 B2
(45) Date of Patent: Sep. 23, 2025

(54) PATIENT-SPECIFIC REGISTRATION JIG AND ASSOCIATED METHOD FOR REGISTERING AN ORTHOPAEDIC SURGICAL INSTRUMENT TO A PATIENT

(71) Applicant: DEPUY SYNTHES PRODUCTS, INC., Raynham, MA (US)

(72) Inventors: Thomas S. Camino, Fort Wayne, IN (US); Barry A. Schnieders, Walkerton, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1101 days.

(21) Appl. No.: 17/362,062

(22) Filed: Jun. 29, 2021

(65) Prior Publication Data
US 2022/0409286 A1    Dec. 29, 2022

(51) Int. Cl.
*A61B 34/20*      (2016.01)
*A61B 17/92*      (2006.01)
(Continued)

(52) U.S. Cl.
CPC .............. *A61B 34/20* (2016.02); *A61B 17/92* (2013.01); *A61B 34/10* (2016.02); *G06T 7/149* (2017.01);
(Continued)

(58) Field of Classification Search
CPC .............. A61B 17/92; A61B 2034/102; A61B 2034/105; A61B 2034/108;
(Continued)

(56) References Cited

U.S. PATENT DOCUMENTS 3,698,017 A    10/1972   Scales et al.
3,840,904 A    10/1974   Tronzo
(Continued)

FOREIGN PATENT DOCUMENTS

CA      2501041 A1    4/2004
CA      2505371 A1    5/2004
(Continued)

OTHER PUBLICATIONS

Berry, Seedhom, et al., "Personalised image-based templates for intra-operative guidance," Proceedings of the Institution of Mechanical Engineers, Part H: Journal of Engineering in Medicine, 111-118, 2005.
(Continued)

*Primary Examiner* — Sameh R Boles
(74) *Attorney, Agent, or Firm* — Barnes & Thornburg LLP

(57) ABSTRACT

A patient-specific registration jig for registering an orthopaedic surgical instrument with a bony anatomy of a patient includes a head and an adaptor coupled to the head. The head includes a patient-specific contact surface configured to contact a portion of the patient's bony anatomy such that the head can be coupled to the patient's bony anatomy in a unique position. The adaptor includes an elongated shank having a first end coupled to the head and a second end and an adaptor end attached to the second end of the elongated shank. The adaptor end is configured to be received by a clutch of the orthopaedic surgical instrument. A method for registering the orthopaedic surgical instrument using the patient-specific registration jig is also disclosed.

10 Claims, 17 Drawing Sheets

(51) Int. Cl.
*A61B 34/10* (2016.01)
*G06T 7/149* (2017.01)
*G06T 7/30* (2017.01)
*G06T 7/70* (2017.01)

(52) U.S. Cl.
CPC .................. *G06T 7/30* (2017.01); *G06T 7/70* (2017.01); *A61B 2034/102* (2016.02); *A61B 2034/105* (2016.02); *A61B 2034/108* (2016.02); *A61B 2034/2055* (2016.02); *G06T 2207/30008* (2013.01)

(58) Field of Classification Search
CPC ... A61B 2034/2055; G06T 7/30; G06T 7/149; G06T 7/70; G06T 2207/30008
See application file for complete search history.

(56) References Cited

U.S. PATENT DOCUMENTS

| | | |
|---|---|---|
| 3,903,549 A | 9/1975 | Deyerle et al. |
| 4,475,549 A | 10/1984 | Oh et al. |
| 4,632,111 A | 12/1986 | Roche et al. |
| 4,711,233 A | 12/1987 | Brown |
| 4,715,860 A | 12/1987 | Amstutz et al. |
| 4,800,874 A | 1/1989 | David et al. |
| 5,007,936 A | 4/1991 | Woolson et al. |
| 5,098,437 A | 3/1992 | Kashuba et al. |
| 5,108,401 A | 4/1992 | Insall et al. |
| 5,133,660 A | 7/1992 | Fenick |
| 5,171,243 A | 12/1992 | Kashuba et al. |
| 5,320,529 A | 6/1994 | Pompa |
| 5,320,625 A | 6/1994 | Bertin et al. |
| 5,658,294 A | 8/1997 | Sederholm et al. |
| 5,768,134 A | 6/1998 | Swaelens et al. |
| 5,817,097 A | 10/1998 | Howard et al. |
| 5,824,085 A | 10/1998 | Sahay et al. |
| 5,931,870 A | 8/1999 | Cuckler et al. |
| 5,942,370 A | 8/1999 | Neckers et al. |
| 5,976,149 A | 11/1999 | Masini et al. |
| 6,019,766 A | 2/2000 | Ling et al. |
| 6,161,080 A | 12/2000 | Aouni et al. |
| 6,228,121 B1 | 5/2001 | Khalili |
| 6,264,698 B1 | 7/2001 | Lawes et al. |
| 6,273,891 B1 | 8/2001 | Masini |
| 6,327,491 B1 | 12/2001 | Franklin et al. |
| 6,344,043 B1 | 2/2002 | Pappas |
| 6,395,005 B1 | 5/2002 | Lovell |
| 6,427,698 B1 | 8/2002 | Yoon |
| 6,463,351 B1 | 10/2002 | Clynch |
| 6,738,657 B1 | 5/2004 | Franklin et al. |
| 6,944,518 B2 | 9/2005 | Roose |
| 6,953,480 B2 | 10/2005 | Mears et al. |
| 6,991,655 B2 | 1/2006 | Iversen |
| 7,534,263 B2 | 5/2009 | Burdulis, Jr. et al. |
| 7,559,931 B2 | 7/2009 | Stone |
| 7,618,451 B2 | 11/2009 | Berez et al. |
| 7,634,119 B2 | 12/2009 | Tsougarakis et al. |
| 7,651,501 B2 | 1/2010 | Penenberg et al. |
| 7,717,956 B2 | 5/2010 | Lang |
| 7,796,791 B2 | 9/2010 | Tsougarakis et al. |
| 7,824,181 B2 | 11/2010 | Sers |
| 7,981,158 B2 | 7/2011 | Fitz et al. |
| 8,133,234 B2 | 3/2012 | Meridew et al. |
| 8,175,683 B2 | 5/2012 | Roose |
| 8,265,949 B2 | 9/2012 | Saddad |
| 8,361,076 B2 | 1/2013 | Roose et al. |
| 8,425,524 B2 | 4/2013 | Aker et al. |
| 8,469,962 B1 | 6/2013 | Head |
| 8,594,395 B2 | 11/2013 | Roose et al. |
| 8,617,170 B2 | 12/2013 | Ashby et al. |
| 8,641,721 B2 | 2/2014 | Aram et al. |
| 8,808,302 B2 | 8/2014 | Roose |
| 8,979,855 B2 | 3/2015 | Aram et al. |
| 8,992,538 B2 | 3/2015 | Keefer |
| 9,131,945 B2 | 9/2015 | Aram et al. |
| 9,138,247 B2 | 9/2015 | Aram et al. |
| 9,168,048 B2 | 10/2015 | Roose |
| 9,299,138 B2 | 3/2016 | Zellner et al. |
| 10,034,753 B2 | 7/2018 | Dressler et al. |
| 10,098,761 B2 | 10/2018 | Sherman et al. |
| 10,149,722 B2 | 12/2018 | Aram et al. |
| 10,251,654 B2 | 4/2019 | Fritzinger |
| 10,278,711 B2 | 5/2019 | Meridew |
| 10,537,343 B2 | 1/2020 | Fritzinger |
| 10,631,878 B2 | 4/2020 | Fritzinger |
| 10,856,891 B2 | 12/2020 | Rhodes et al. |
| 10,874,404 B2 | 12/2020 | Langhorn et al. |
| 11,051,829 B2 | 7/2021 | Courtis et al. |
| 11,090,085 B2 | 8/2021 | Rhodes et al. |
| 11,134,908 B2 | 10/2021 | Pollock et al. |
| 11,229,519 B2 | 1/2022 | Radermacher et al. |
| 11,304,710 B2 | 4/2022 | Rhodes et al. |
| 11,348,216 B2 | 5/2022 | Pollock et al. |
| 2002/0007294 A1 | 1/2002 | Bradbury et al. |
| 2004/0152970 A1 | 8/2004 | Hunter et al. |
| 2004/0204760 A1 | 10/2004 | Fitz et al. |
| 2004/0236424 A1 | 11/2004 | Berez et al. |
| 2005/0107799 A1 | 5/2005 | Graf et al. |
| 2005/0148843 A1 | 7/2005 | Roose |
| 2005/0234461 A1 | 10/2005 | Burdulis et al. |
| 2005/0267584 A1 | 12/2005 | Burdulis et al. |
| 2006/0129160 A1 | 6/2006 | Liu et al. |
| 2007/0106305 A1 | 5/2007 | Kao et al. |
| 2007/0198022 A1 | 8/2007 | Lang et al. |
| 2007/0276400 A1 | 11/2007 | Moore et al. |
| 2008/0009874 A1 | 1/2008 | Meridew et al. |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0234665 A1 | 9/2008 | Godara et al. |
| 2008/0234685 A1 | 9/2008 | Gjerde |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0306558 A1 | 12/2008 | Hakki |
| 2009/0088674 A1 | 4/2009 | Caillouette et al. |
| 2009/0131941 A1 | 5/2009 | Park et al. |
| 2009/0138020 A1 | 5/2009 | Park et al. |
| 2009/0149977 A1 | 6/2009 | Schendel |
| 2009/0163922 A1 | 6/2009 | Meridew et al. |
| 2009/0222014 A1 | 9/2009 | Bojarski et al. |
| 2009/0270868 A1 | 10/2009 | Park et al. |
| 2009/0307893 A1 | 12/2009 | Burdulis, Jr. et al. |
| 2010/0016984 A1 | 1/2010 | Trabish |
| 2010/0023015 A1 | 1/2010 | Park |
| 2010/0042105 A1 | 2/2010 | Park et al. |
| 2010/0082035 A1 | 4/2010 | Keefer |
| 2010/0087829 A1 | 4/2010 | Metzger et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217338 A1 | 8/2010 | Carroll et al. |
| 2010/0274253 A1 | 10/2010 | Ure |
| 2011/0015639 A1 | 1/2011 | Metzger et al. |
| 2011/0213431 A1 | 9/2011 | Fitz et al. |
| 2011/0224674 A1 | 9/2011 | White et al. |
| 2012/0123423 A1 | 5/2012 | Fryman |
| 2013/0046310 A1 | 2/2013 | Ranawat et al. |
| 2013/0150862 A1 | 6/2013 | Aram et al. |
| 2014/0276872 A1* | 9/2014 | Song .................. A61F 2/30942 606/91 |
| 2014/0336657 A1 | 11/2014 | Iannotti et al. |
| 2015/0148807 A1 | 5/2015 | Park |
| 2016/0287337 A1 | 10/2016 | Aram et al. |
| 2016/0317312 A1 | 11/2016 | Bojarski et al. |
| 2017/0164957 A1 | 6/2017 | Bojarski et al. |
| 2017/0325892 A1* | 11/2017 | Aghazadeh ........ A61B 17/8897 |

(56) References Cited

U.S. PATENT DOCUMENTS

| | | | |
|---|---|---|---|
| 2018/0168740 | A1 | 6/2018 | Ryan et al. |
| 2020/0163721 | A1 | 5/2020 | Aghazadeh |
| 2022/0233320 | A1* | 7/2022 | Wismayer ............. A61F 2/34 |

FOREIGN PATENT DOCUMENTS

| | | |
|---|---|---|
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| CN | 101711695 A | 5/2010 |
| DE | 2830566 A1 | 1/1980 |
| DE | 4219939 A1 | 12/1993 |
| EP | 645984 A1 | 4/1995 |
| EP | 756735 | 2/1997 |
| EP | 1486900 A1 | 12/2004 |
| EP | 1669033 A1 | 6/2006 |
| GB | 2426200 A | 11/2006 |
| JP | 2005-511238 A | 4/2005 |
| JP | 2010-82448 A | 4/2010 |
| KR | 2005072500 A | 7/2005 |
| KR | 2005084024 A | 8/2005 |
| TW | I231755 B | 5/2005 |
| WO | 1993025157 A1 | 12/1993 |
| WO | 9528688 A1 | 10/1995 |
| WO | 2001084479 A1 | 11/2001 |
| WO | 2005027755 A1 | 3/2005 |
| WO | 2004049981 A3 | 4/2005 |
| WO | 2005051239 A1 | 6/2005 |
| WO | 2005051240 A1 | 6/2005 |
| WO | 2005084558 A1 | 9/2005 |
| WO | 2006058057 A2 | 6/2006 |
| WO | 2006060795 A1 | 6/2006 |
| WO | 2007041375 A2 | 4/2007 |
| WO | 2007092841 A2 | 8/2007 |
| WO | 2007097854 A2 | 8/2007 |
| WO | 2007145937 A2 | 12/2007 |
| WO | 2008014618 A1 | 2/2008 |
| WO | 2008021494 A2 | 2/2008 |
| WO | 2008112996 A1 | 9/2008 |
| WO | 2009045960 A1 | 4/2009 |
| WO | 2009111512 A2 | 9/2009 |
| WO | 2009001083 A1 | 12/2009 |
| WO | 2010030809 | 3/2010 |
| WO | 2012/021264 | 2/2012 |
| WO | 2017204832 | 11/2017 |

OTHER PUBLICATIONS

SurgiTAIX AG, "OrthoTAIX for Orthopaedic Surgery." Available at http://www.surgitaix.com/Products/OrthoTAIX/OrthoTAIX.pdf.
Radermacher et al., "Computer-Integrated Orthopaedic Surgery: Connection of Planning and Execution in Surgical Intervention," Computer Integrated Surgery, 451-463, 1995.
Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P Nolte and R. Ganz, eds, 42-52, Hogrefe & Huber Publishing 1999.
PCT Search Report for International Application No. PCT/US2011/044466, filed Jul. 19, 2011, 4 pages.
Radermacher et al., "Computer Assisted Orthopaedic Surgery with Image Based Individual Templates", Clin Orthopaedics and Related Research 354, 28-38, 1998, 11 pages.
Hafez et al., "Computer-assisted Total Knee Arthroplasty Using Patient-Specific Templating", Clinical Orthopaedics and Related Research, 444, 184-192, 2006 (9 pages).
"Insall/Burstein II Surgical Technique", Constrained Condylar Modular Knee System, Zimmer, 1989, (18 pages).
PCT Search Report for Application PCT/US2008/078143, Dec. 19, 2008, (17 pages).
International Preliminary Report on Patentability for International Patent Publication No. PCT/US2008/078143, Apr. 15, 2010, 8 pages.
European Search Report for European Patent Application No. 10150487.6-2310, May 12, 2010, 7 pages.
European Search Report for European Patent Application No. 09171188.7-2310, Sep. 24, 2010, 7 pages.
Customized Patient Instruments, Patient specific instruments for patient specific needs, brochure. (2008) DePuy Orthopaedics, Inc. 14 sheets.
Customized Patient Instruments, Primary Cruciate Retaining Surgical Technique for use with the Sigma.RTM. Knee System Utilizing Specialist.RTM. 2 Instrumentation, brochure. (2008) DePuy Orthopaedics, Inc. pp. 1-23.
"TruMatch.™. Personalized knee replacement solutions," tri-fold brochure. (2009) SIGMA.RTM. DePuy Orthopaedics, Inc. 2 pages.
Murphy, S.B., et al. "The Hip Sextant: Navigation of Acetabular Component Orientation Using a Mechanical Instrument," brochure. (2009) 1 page.
Seel et al., "Three-Dimensional Planning and Virtual Radiographs in Revision Total Hip Arthroplasty for Instability", Clinical Orthopaedics and Related Research, No. 442, pp. 35-38, Jan. 2006.
Radermacher, "Development of a Clinical Demonstrater for Computer Assisted Orthopedic Surgery with CT-Image Based Individual Templates (chapter in Computer Assisted Radiology and Surgery, edited by H.U. Lemke, M.W. Vannier and K. Inamura)," (1997).
Radermacher, "Clinical Experience With the Individual Template Technique," (2001).
Radermacher, "Computer Assisted Orthopedic Surgery by Means of Individual Templates Aspects and Analysis of Potential Applications," (1994).
Radermacher, German Version "Potentials of CT-based Planning and Template-based Procedure in Hip and Knee Surgery," (2000).
Radermacher, English Translation of German Version "Potentials of CT-based Planning and Template-based Procedure in Hip and Knee Surgery," (2000).
Patent Cooperation Treaty, International Preliminary Report on Patentability, International Application No. PCT/US2011/044466, Dated Feb. 12, 2013, 10 Pages.
English translation of Japanese Search Report issued Feb. 24, 2015 in application 2013-524085, 4 pages.
English translation of First Office Action issued by the State Intellectual Property Office, P.R. China, for Chinese Application No. 201180039293.9, Jan. 6, 2015, 10 pages.
English translation of Chinese Search Report for Chinese Application No. 201180039293.9, Dec. 28, 2014, 2 pages.
Biomet: Signature Hip Technology Personalized Patient Care, available online, accessed Feb. 23, 2016, 2 pages.
International Search Report, International Application No. PCT/US2016/057260, 2 pages.
International Search Report and Written Opinion, International Application No. PCT/US2016/057260, dated May 3, 2017, 10 pages.
International Search Report and Written Opinion, Application PCT/IB2022/055850, completed Sep. 28, 2022, 22 pages.

* cited by examiner

PATIENT-SPECIFIC REGISTRATION JIG AND ASSOCIATED METHOD FOR REGISTERING AN ORTHOPAEDIC SURGICAL INSTRUMENT TO A PATIENT

TECHNICAL FIELD

The present disclosure relates generally to customized patient-specific orthopaedic surgical instruments and more particularly to a patient-specific registration jig for registering orthopaedic surgical instruments to a patient's bony anatomy.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral component prosthesis. The acetabular prosthetic component is implanted into the patient's acetabulum and generally includes an outer shell configured to engage the acetabulum and an inner bearing or cup liner coupled to the shell. The femoral component prosthesis is implanted into the patient's femur and generally includes a stem component embedded into the medullary canal the femur and a femoral head component. The femoral head component is configured to engage with and articulate in the cup liner of the acetabular to form a ball and socket joint that approximates the natural hip joint.

To facilitate the replacement of a patient's natural joint (e.g., the patient's hip joint) with an orthopaedic prosthesis, orthopaedic surgeons may use a variety of orthopaedic surgical instruments such as, for example, reamers, drill, broaches, impactors, and/or other surgical instruments. In some situations, such as during computer assisted orthopaedic surgery and/or surgical navigation, the position of the orthopaedic surgical instruments relative to the patient anatomy may be tracked and, in some cases, visualized for the orthopaedic surgeon.

SUMMARY

According to an aspect of the present disclosure, a patient-specific registration jig for registering an orthopaedic surgical instrument with the bony anatomy of a patient includes a head and an adaptor coupled to the head and extending longitudinally therefrom. The head includes a patient-specific contact surface configured to contact a portion of the patient's bony anatomy. The patient-specific contact surface includes a patient-specific negative contour configured to receive a portion of the patient's bony anatomy. The adaptor includes an elongated shank having a first end coupled to the head and a second end and an adaptor end attached to the second end of the elongated shank and configured to be received by a clutch of the orthopaedic surgical instrument.

In some embodiments, the patient-specific negative contour is configured to receive a portion of the patient's bony anatomy such that the head is configured to couple to that portion of the patient's bony anatomy in a unique orientation and position relative to the patient's bony anatomy.

Additionally, in some embodiments, the patient-specific registration jig may be embodied as a patient-specific acetabulum registration jig and the patient-specific contact surface is configured to contact an acetabulum of the patient's bony anatomy. In such embodiments, the patient-specific contact surface may include a patient-specific negative contour configured to receive a portion of the interior bony surface of the acetabulum of the patient's bony anatomy. Alternatively, in other embodiments, the patient-specific registration jig may be embodied as a patient-specific femoral registration jig and the patient-specific contact surface is configured to contact a femur of the patient's bony anatomy. In such embodiments, the patient-specific contact surface may include a patient-specific negative contour configured to receive a portion of a greater trochanter of the patient's femur.

In some embodiments, the adaptor end may include a first keyed feature configured to mate with a second keyed feature of the clutch of the orthopaedic surgical instrument. Additionally, in some embodiments, the patient-specific registration jig may further include a tracking sensor configured for interaction with an orthopaedic surgical navigation system to facilitate tracking of a position of the patient-specific registration jig.

According to another aspect of the present disclosure, a system for registering an orthopaedic surgical instrument with a bony anatomy of a patient includes a patient-specific registration jig and an orthopaedic surgical instrument. The patient-specific registration jig includes a head and an adaptor coupled to the head and extending longitudinally therefrom. The head includes a patient-specific contact surface configured to contact a portion of the patient's bony anatomy, and the patient-specific contact surface includes a patient-specific negative contour configured to receive a portion of the patient's bony anatomy. The adaptor includes an elongated shank having a first end coupled to the head and a second end and an adaptor end attached to the second end of the elongated shank.

The orthopaedic surgical instrument includes a clutch and at least one tracking sensor. The clutch may be configured to receive the adaptor end of the adaptor of the patient-specific registration jig and is operable to secure the patient-specific registration jig to the orthopaedic surgical instrument. The tracking sensor is configured for interaction with a surgical navigation system to facilitate tracking of the orthopaedic surgical instrument.

In some embodiments, the patient-specific negative contour of the patient-specific registration jig may be configured to receive a portion of the patient's bony anatomy such that the head of the patient-specific registration jig is configured to couple to that portion of the patient's bony anatomy in a unique orientation and position relative to the patient's bony anatomy. Additionally, in some embodiments, the patient-specific registration jig may be embodied as a patient-specific acetabulum registration jig, and the patient-specific contact surface may include a patient-specific negative contour configured to receive a portion of the interior bony surface of the acetabulum of the patient's bony anatomy. Alternatively, in other embodiments, the patient-specific registration jig is a patient-specific femoral registration jig, and the patient-specific contact surface includes a patient-specific negative contour configured to receive a portion of a greater trochanter of the patient's femur.

Additionally, in some embodiments, the adaptor end may include a first keyed feature configured to mate with a second keyed feature of the clutch of the orthopaedic surgical instrument. Furthermore, in some embodiments, the orthopaedic surgical instrument may be an orthopaedic impactor. For example, the orthopaedic surgical instrument may be embodied as an orthopaedic automated impactor. Additionally, in some embodiments, the tracking sensor may be embodied as an electrical sensor configured to wirelessly communicate with the navigation system or as an optical tracking sensor.

According to yet a further aspect of the present disclosure, a method for registering an orthopaedic surgical instrument with a bony anatomy of a patient may include attaching a patient-specific registration jig to an orthopaedic surgical instrument. The patient-specific registration jig may include a head and an adaptor coupled to the head and extending longitudinally therefrom. The head may include a patient-specific contact surface configured to contact a portion of the patient's bony anatomy, and the patient-specific contact surface may include a patient-specific negative contour configured to receive a portion of the patient's bony anatomy. Additionally, the adaptor may be configured to be received by a clutch of the orthopaedic surgical instrument.

The method may also include coupling the patient-specific registration jig to a portion of the patient's bony anatomy. In some embodiments, coupling the patient-specific registration jig may include inserting the portion of the patient's bony anatomy into the patient-specific negative contour of the head of the patient-specific registration jig. The method may further include controlling a surgical navigation system to register the orthopaedic surgical instrument to the bony anatomy of the patient while the patient-specific registration jig is coupled to the patient's bony anatomy.

In some embodiments, controlling the surgical navigation system to register the orthopaedic surgical instrument may include controlling the surgical navigation system to generate registration data indicative of a position of the orthopaedic surgical instrument relative to the patient's bony anatomy. Additionally, in some embodiments, the method may further include controlling the surgical navigation system to track a position of the orthopaedic surgical instrument based on data received from a tracking sensor coupled to the orthopaedic surgical instrument.

BRIEF DESCRIPTION OF THE DRAWINGS

The detailed description particularly refers to the following figures, in which.

DETAILED DESCRIPTION OF THE DRAWINGS

Figure 1:
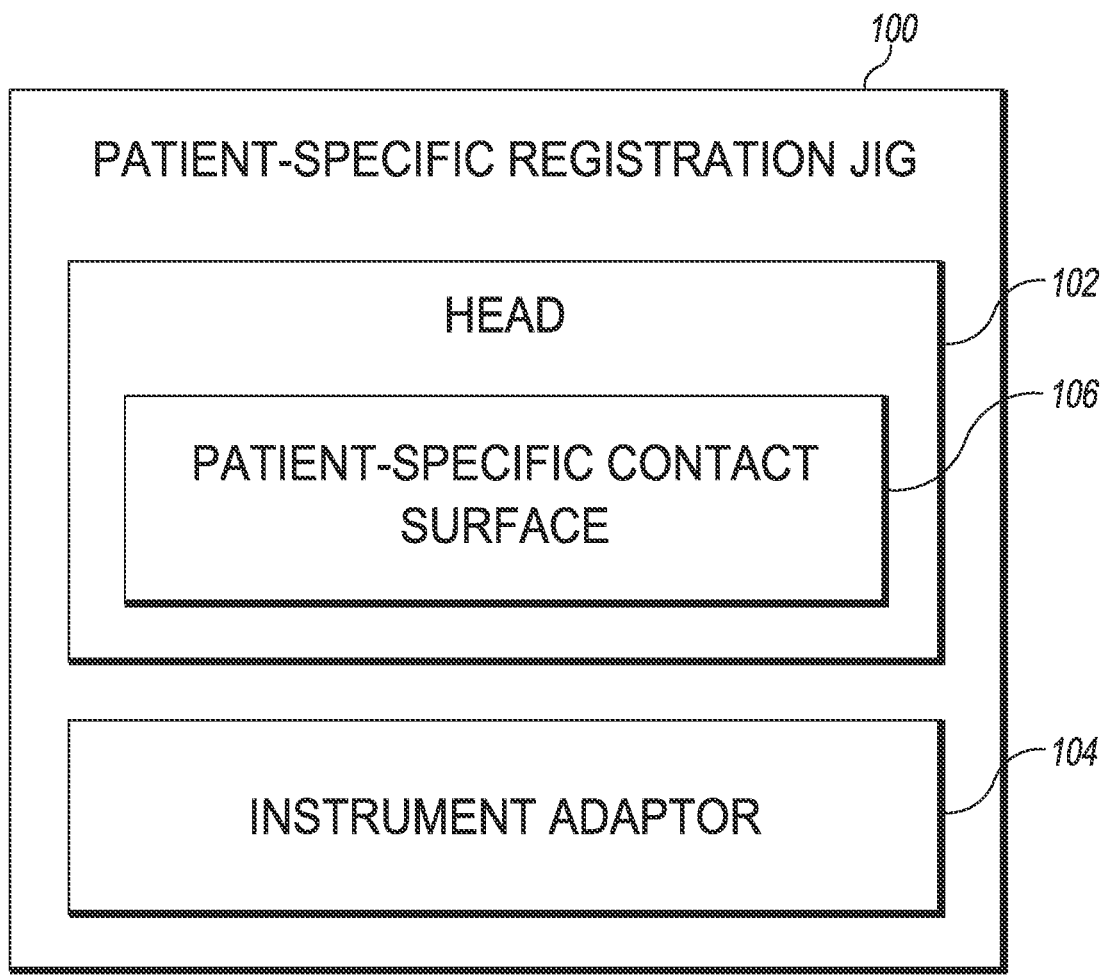
FIG. 1 is a simplified block diagram of an embodiment of a patient-specific registration jig for registering an orthopaedic surgical instrument with a patient's bony anatomy.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and/or surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative patient-specific registration jig 100 includes a head 102 and an adaptor 104 coupled to the head 102. As discussed in more detail below, the patient-specific registration jig 100 is usable by an orthopaedic surgeon to register an orthopaedic surgical instrument (e.g., an impactor) with the bony anatomy of the patient (e.g., with a coordinate system defined by the patient's bony anatomy). It should be appreciated that such registration, allows the orthopaedic surgeon to track the location of the orthopaedic surgical instrument(s) relative to the patient's bony anatomy and, ultimately, ensure proper alignment of the final implant. For example, by using a registered implant impactor, the orthopaedic surgeon can ensure the final acetabular implant is located and oriented properly (e.g., proper inclination and version) according to a surgical plan and/or the orthopaedic surgeon's preference.

To facilitate the registration process, the head 102 of the patient-specific registration jig 100 includes a patient-specific contact surface 106 configured to couple to a particular portion of the patient's bony anatomy in a unique location and orientation. That is, as described in more detail below, the patient-specific contact surface 106 includes a patient-specific negative contour that matches and is configured to receive a portion of the contour of that particular portion of the patient's bony anatomy.

It should be further appreciated that the registration jig 100 is "patient-specific" in that the registration jig 100 is intended, and configured, for use on a particular patient. As such, as used herein, the term "patient-specific registration jig" is distinct from standard, non-patient specific registration jigs or other surgical tools that are intended for use on a variety of different patients.

In some embodiments, the patient-specific registration jig 100 may be customized to the particular patient based on the location at which the jig 100 is to be coupled to one or more bones of the patient, such as the interior surface of the patient's acetabulum, the area of the patient's coxal bone proximate to the acetabulum, the greater trochanter of a femur of the patient, and so forth. As such, the patient-specific contact surface 106 forms a bone-contacting or facing surface that has a negative contour that matches the contour of that particular portion of the patient's bony anatomy. That is, the negative contour of the patient-specific contact surface 106 is configured to receive a matching "positive" contour surface of the relevant portion of the patient's bony anatomy (e.g., the interior surface of the patient's acetabulum). As such, the orthopaedic surgeon's guesswork and/or intra-operative decision-making with respect to the placement of the patient-specific registration jig 100 on the patient's bony anatomy is reduced. For example, the orthopaedic surgeon may not be required to locate landmarks of the patient's bone to facilitate the placement of the patient-specific registration jig 100, which typically requires some amount of estimation on part of the surgeon. Rather, the orthopaedic surgeon may simply couple the patient-specific registration jig 100 to the patient's bony anatomy in the unique location.

As discussed above, the adaptor 104 is coupled to the head 102 and extends therefrom. Additionally, as discussed in more detail below, the adaptor 104 is configured to be coupled to the orthopaedic surgical instrument that is to be registered to the patient's bony anatomy. For example, the adaptor 104 may include an adaptor end, keyed features, and/or other mechanisms configured to be received by the orthopaedic surgical instrument to facilitate the attachment of the patient-specific registration jig 100 to the orthopaedic surgical instrument to be registered.

Figure 2:
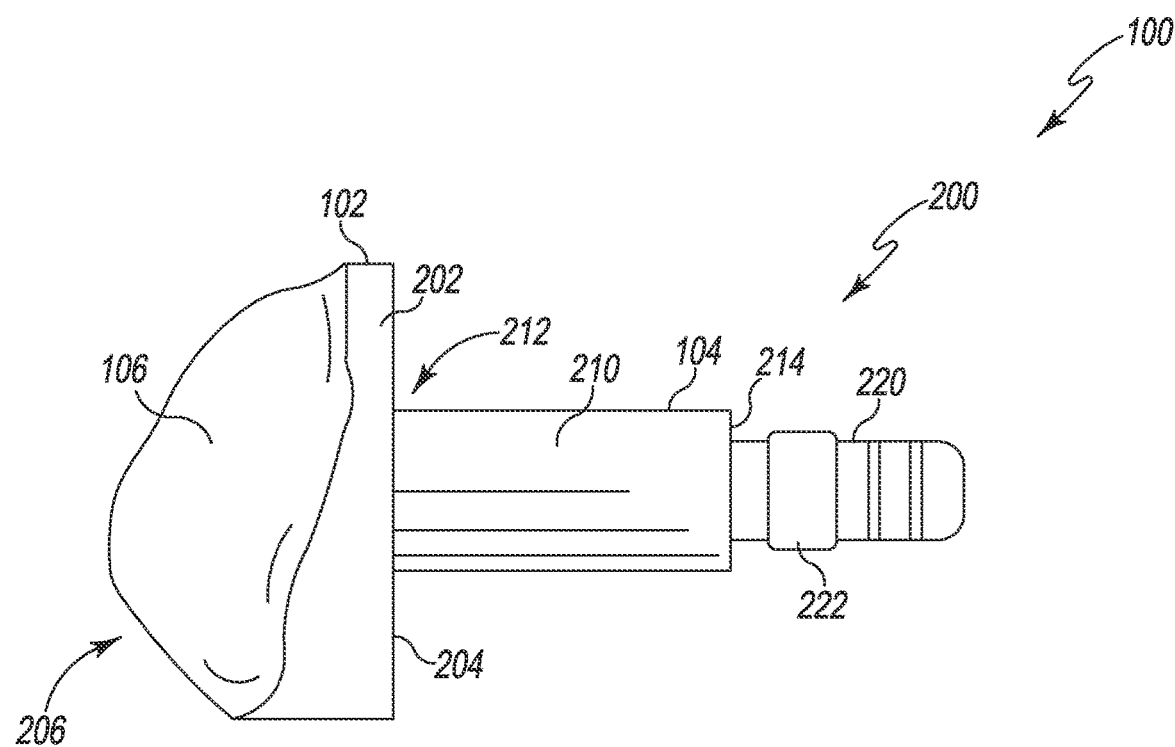
FIG. 2 is an elevation view of an embodiment of the patient-specific registration jig of FIG. 1 embodied as an acetabulum registration jig.
Figure 3:
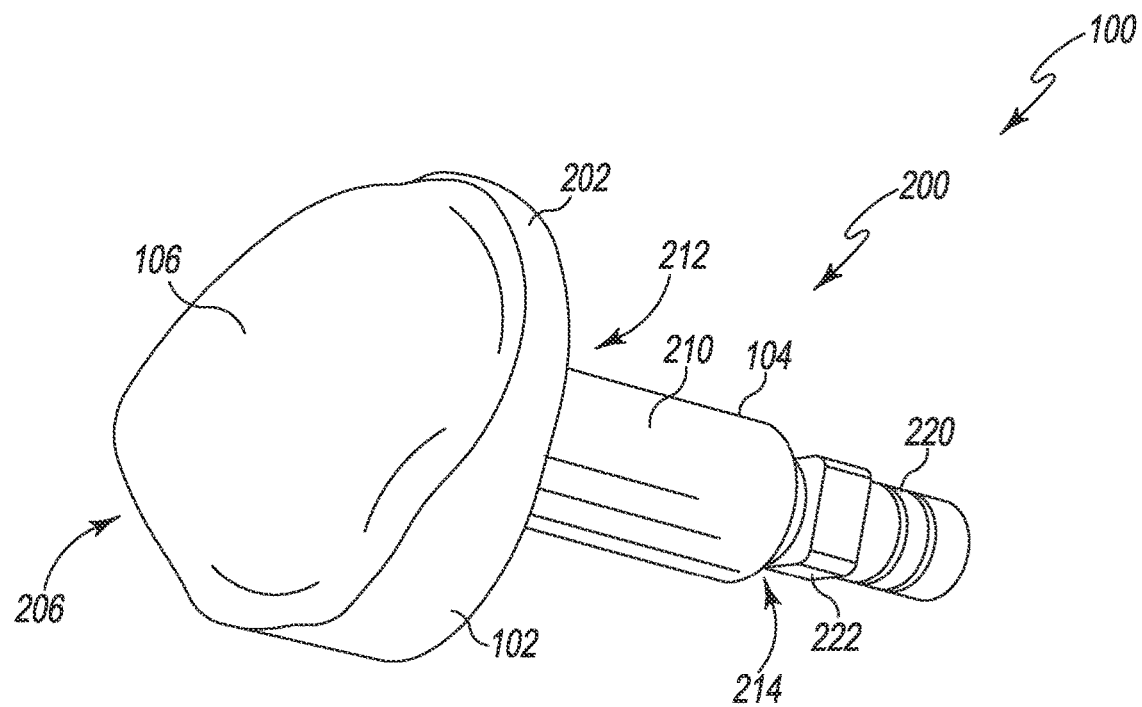
FIG. 3 is a proximal perspective view of the patient-specific registration jig of FIG. 2 showing a patient-specific surface of the acetabulum registration jig.

Referring now to FIGS. 2 and 3, in some embodiments, the patient-specific registration jig 100 may be embodied as a patient-specific acetabulum registration jig 200. The patient-specific acetabulum registration jig 200 includes the head 102 and the adaptor 104 coupled to the head 102 and extending longitudinally therefrom. The head 102 of the patient-specific acetabulum registration jig 200 is generally cylindrical in shape and includes a base 202 having a distal side 204 and a proximal side 206. The patient-specific contact surface 106 is defined on the proximal side 206 of the base 202. The patient-specific acetabulum registration jig 200 is configured for use in the acetabulum of the patient and, as such, the patient-specific contact surface 106 of the patient-specific acetabulum registration jig 200 is configured to contact the bony interior surface of the patient's acetabulum. As such, the patient-specific contact surface 106 of the patient-specific acetabulum registration jig 200 includes a negative contour that matches the contour of the patient's acetabulum such that the patient-specific acetabulum registration jig 200 is configured to be inserted into, or otherwise coupled to, the patient's acetabulum in a single, unique position (i.e., a unique orientation and location).

Figure 4:
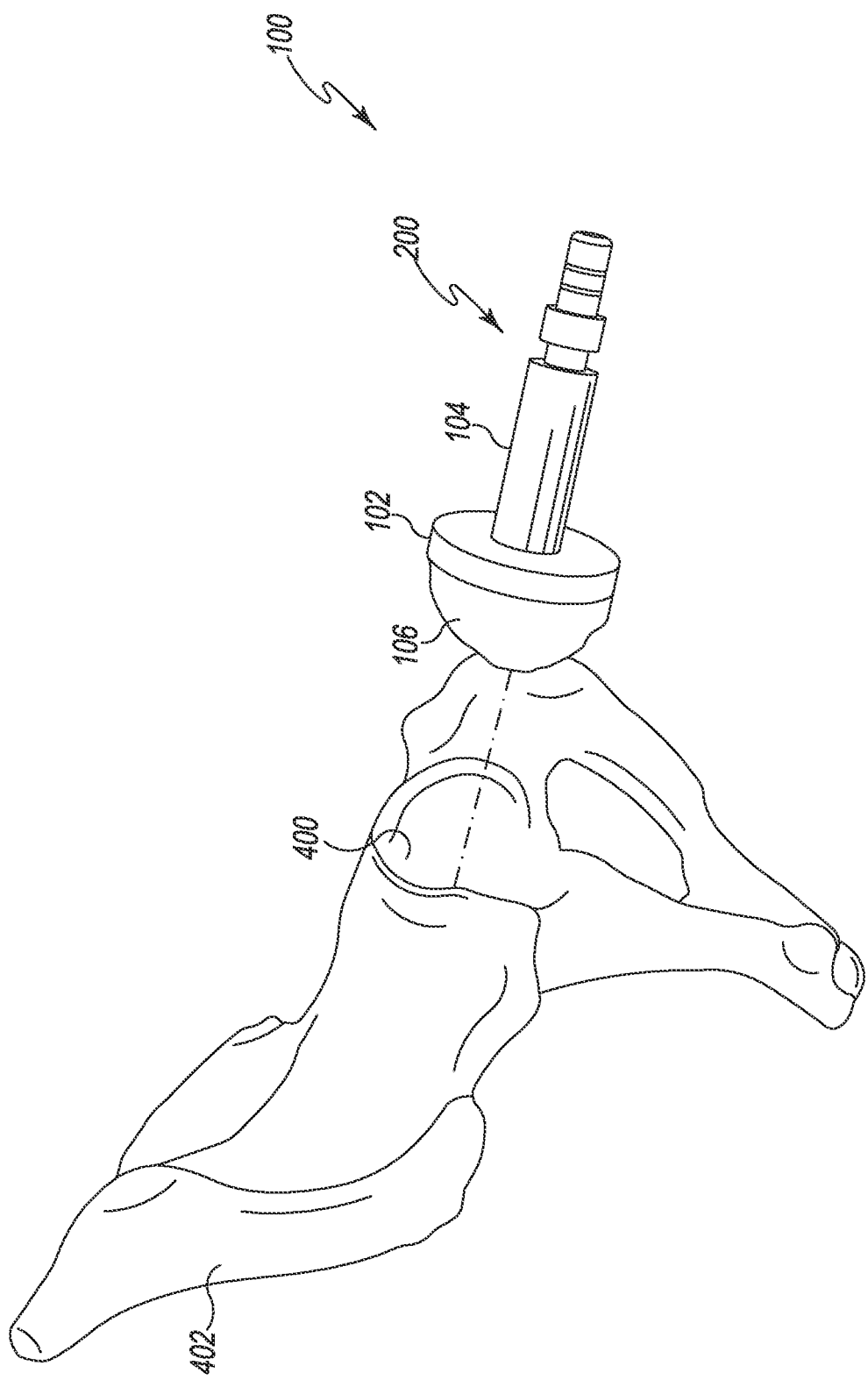
FIG. 4 is a perspective view of the patient-specific registration jig of FIG. 2 being inserted into an acetabulum of a patient's bony anatomy.
Figure 5:
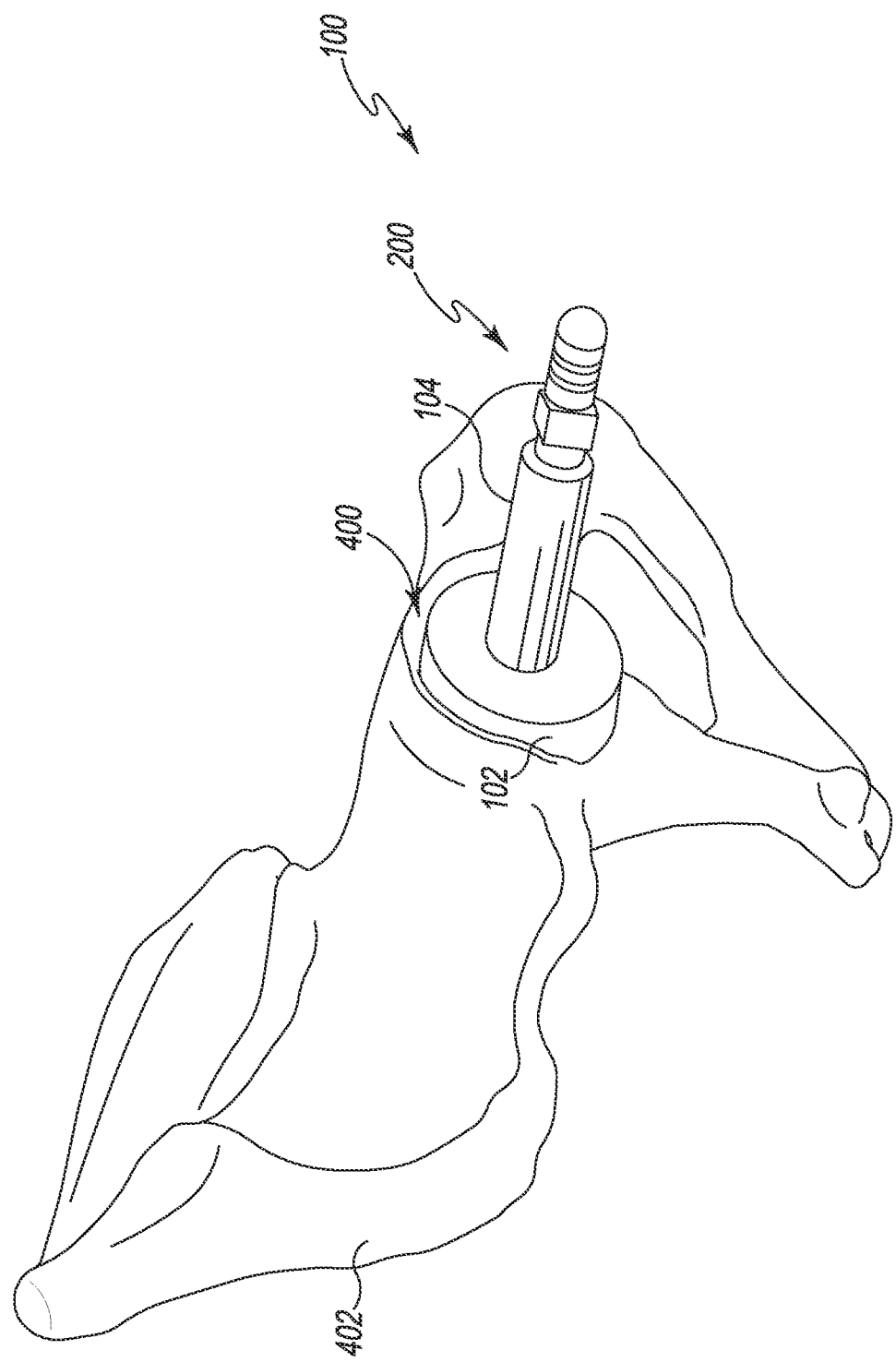
FIG. 5 is a perspective view of the patient-specific registration jig of FIG. 4 fully received in the acetabulum of the patient such that the patient-specific surface of the patient-specific registration jig is in contact with the interior surface of the patient's acetabulum.

As shown in FIG. 4, an orthopaedic surgeon may couple the patient-specific acetabulum registration jig 200 to an acetabulum 400 of a patient's hipbone 402 by aligning the patient-specific acetabulum registration jig 200 with the patient's acetabulum 400 and moving the patient-specific acetabulum registration jig 200 into contact with the acetabulum 400. Because the patient-specific contact surface 106 of the patient-specific acetabulum registration jig 200 is configured to receive a corresponding contour of the patient's acetabulum 400, the patient-specific acetabulum registration jig 200 will seat into, or otherwise couple to, the patient's acetabulum 400 in a singular, unique orientation and location as shown in FIG. 5. As such, the patient-specific acetabulum registration jig 200 is configured to be inserted or coupled to the patient's acetabulum 400 in a known position relative to the patient's bony anatomy, which facilitates the registration of orthopaedic surgical instruments attached to the patient-specific acetabulum registration jig 200 to the patient's bony anatomy.

Referring back to FIGS. 2 and 3, the adaptor 104 of the patient-specific acetabulum registration jig 200 includes a shank 210 having a proximal end 212 attached to the distal side 204 of the base 202 of the head 102 and a distal end 214, which is opposite the proximal end 212. An adaptor end 220 of the adaptor 104 is formed at, or otherwise coupled to, the distal end 214 of the shank 210. The adaptor end 220 is configured to be coupled to the orthopaedic surgical instrument to be registered to the patient's bony anatomy. For example, the adaptor end 220 may be configured to be received in a clutch or other receiver of the orthopaedic surgical instrument, which may be operable to secure the patient-specific acetabulum registration jig 200 to orthopaedic surgical instrument. In some embodiments, for example, the adaptor end 220 may include keyed features 222 to facilitate attachment to the orthopaedic surgical instrument (e.g., the clutch of the orthopaedic surgical instrument may be configured to mate with the keyed features 222 of the adaptor end 220).

Figure 6:
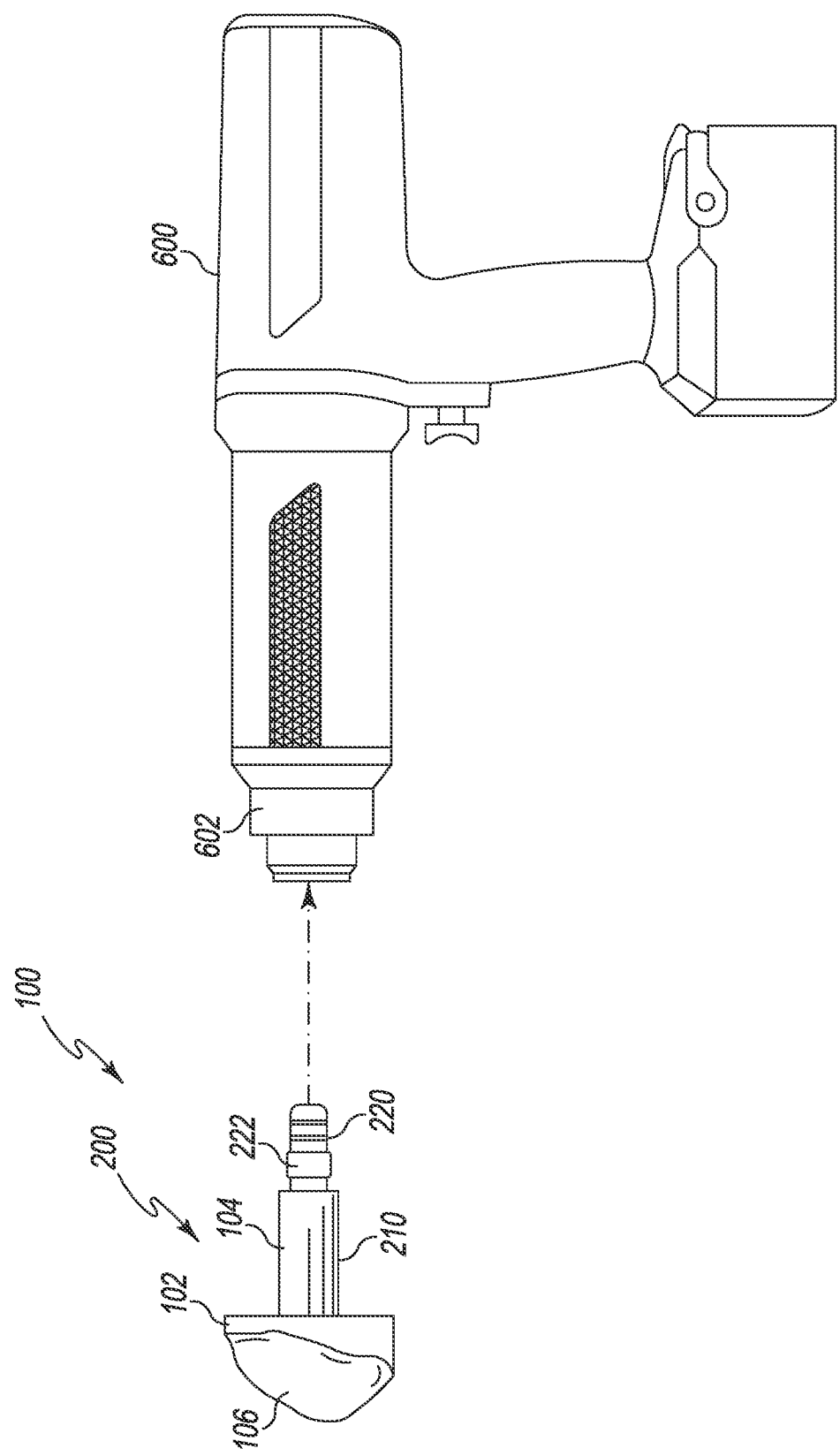
FIG. 6 is an elevation view of the patient-specific registration jig of FIG. 2 being coupled to an orthopaedic surgical instrument embodied as an automatic impactor.

For example, as shown in FIG. 6, an orthopaedic surgeon may couple the patient-specific acetabulum registration jig 200 to an orthopaedic surgical instrument, illustratively embodied as an automated surgical impactor 600. The automated surgical impactor 600 may be embodied as a Kincise™ surgical automated system component commercially available from DePuy Synthes of Warsaw, Indiana. To couple the patient-specific acetabulum registration jig 200 to the automated impactor 600, the orthopaedic surgeon may insert the adaptor end 220 of the adaptor 104 of the patient-specific acetabulum registration jig 200 into a clutch 602 of the automated impactor 600. The orthopaedic surgeon may secure the patient-specific acetabulum registration jig 200 to the automated impactor 600 by adjusting the clutch 602 and/or using another locking mechanism of the automated impactor 600 and/or a separate locking device to secure the jig 200 to the impactor 600.

Figure 7:
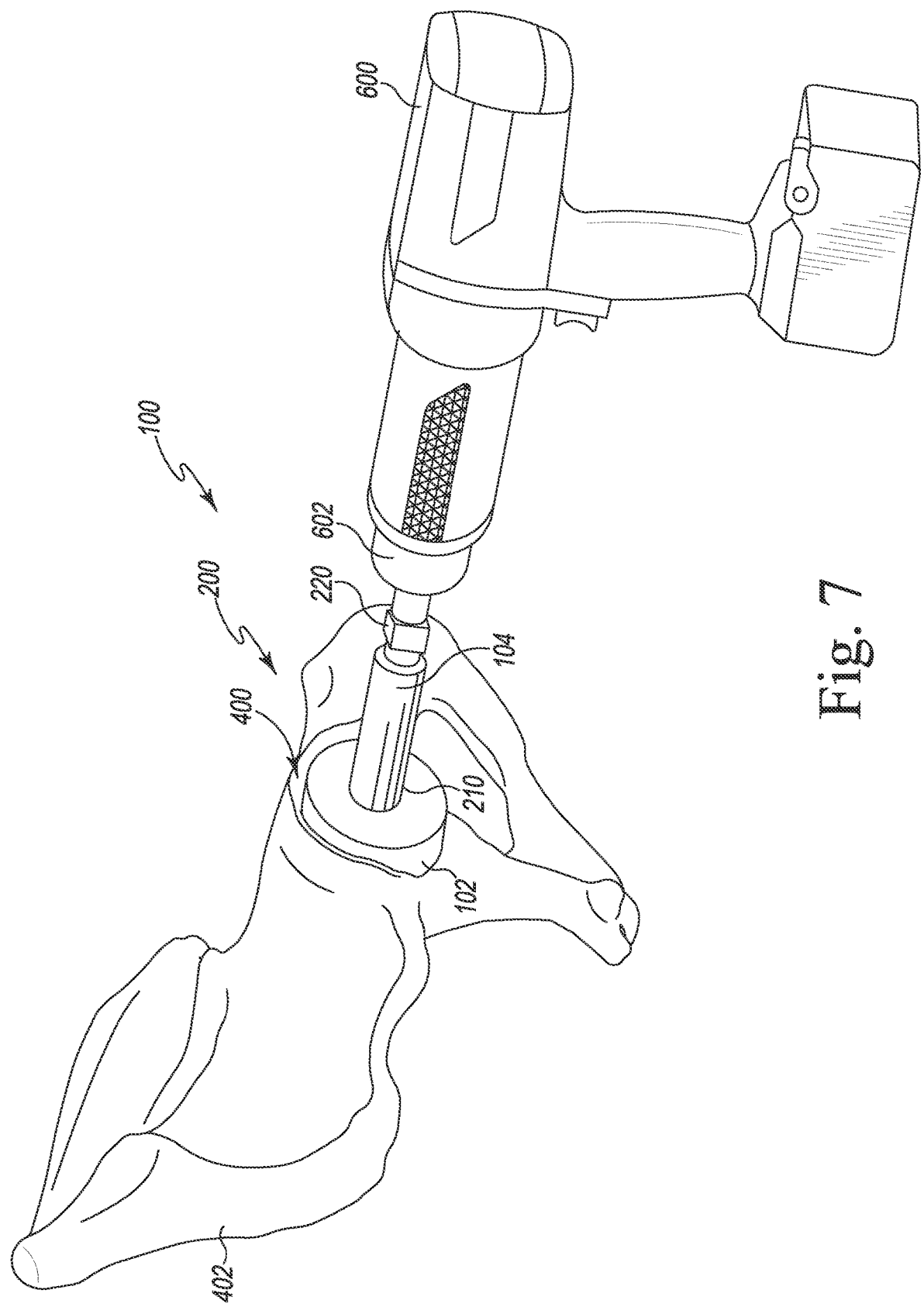
FIG. 7 is a perspective view of the assembled orthopaedic surgical instrument and patient-specific registration jig of FIG. 6 with the patient-specific registration jig being received in the acetabulum of the patient such that the patient-specific surface of the patient-specific registration jig is in contact with the interior surface of the patient's acetabulum.

After the orthopaedic surgeon has secured the patient-specific registration jig 200 to the automated impactor 600, the orthopaedic surgeon may couple the patient-specific registration jig 200 to the acetabulum 400 of the patient by aligning the patient-specific acetabulum registration jig 200 with the patient's acetabulum 400 and moving the patient-specific acetabulum registration jig 200 into contact with the acetabulum 400. Again, because the patient-specific contact surface 106 of the patient-specific acetabulum registration jig 200 is configured to receive a corresponding contour of the patient's acetabulum 400, the patient-specific acetabulum registration jig 200 will seat into, or otherwise couple to, the patient's acetabulum 400 in a singular, unique orientation and location as shown in FIG. 7, with the automated impactor 600 attached. As such, the patient-specific acetabulum registration jig 200 is configured to be inserted or coupled to the patient's acetabulum 400 in a known position relative to the patient's bony anatomy, which facilitates the registration of the automated impactor 600 attached to the patient-specific acetabulum registration jig 200 to the patient's bony anatomy as discussed in more detail below.

Figure 8:
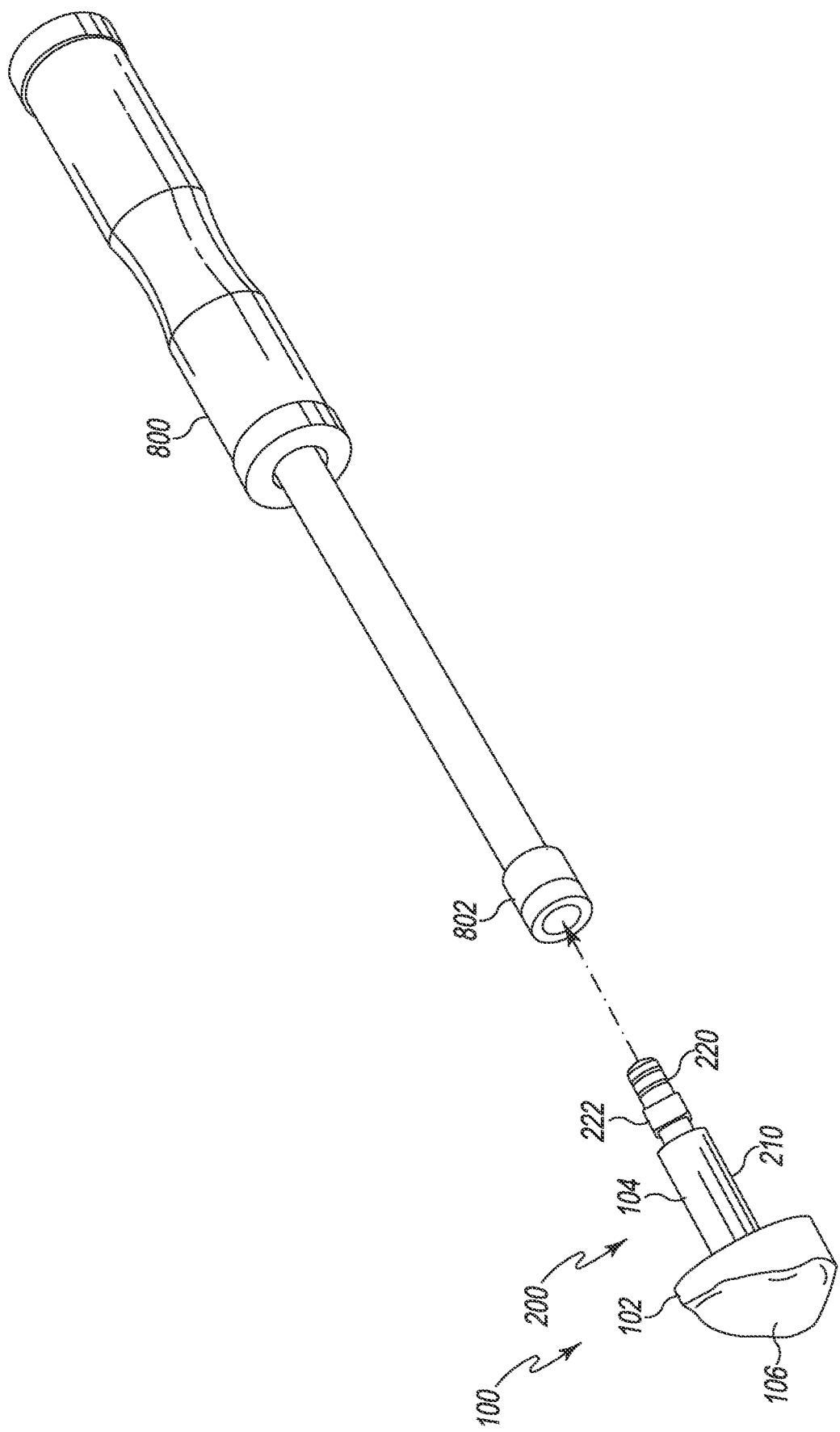
FIG. 8 is an elevation view of the patient-specific registration jig of FIG. 2 being coupled to another orthopaedic surgical instrument embodied as a manual impactor.

Of course, the patient-specific acetabulum registration jig 200 may be used with other types of orthopaedic surgical instruments. For example, as shown in FIG. 8, the orthopaedic surgeon may couple the patient-specific acetabulum registration jig 200 to a manual surgical impactor 800. To do so, the orthopaedic surgeon may insert the adaptor end 220 of the adaptor 104 of the patient-specific acetabulum registration jig 200 into a clutch 802 of the manual impactor 800. Similar to the automated impactor 600, the orthopaedic surgeon may secure the patient-specific registration jig 200 to the manual impactor 800 by adjusting the clutch 802 and/or using another locking mechanism of the manual impactor 800 and/or a separate locking device to secure the jig 200 to the impactor 800.

Figure 9:
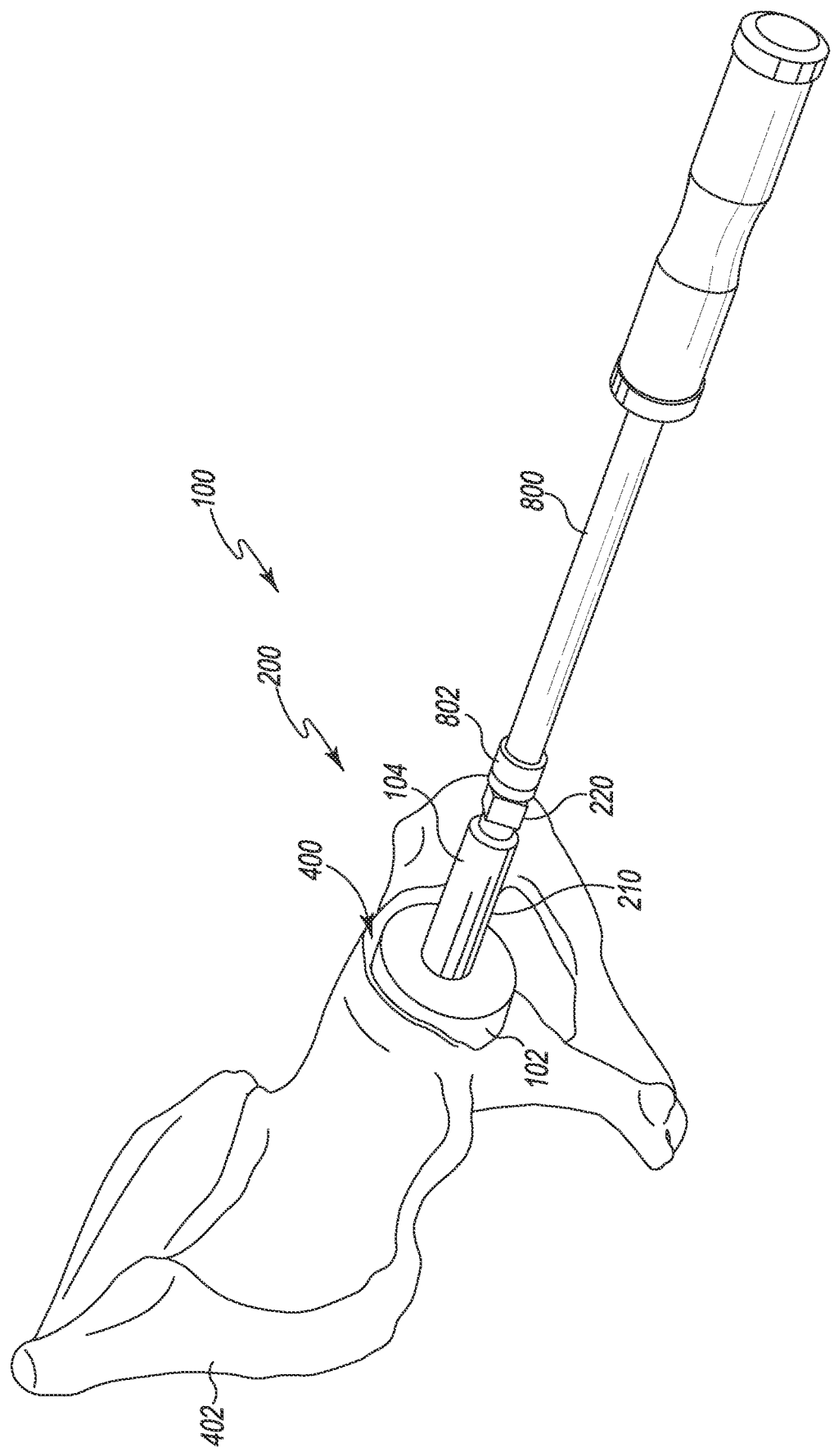
FIG. 9 is a perspective view of the assembled orthopaedic surgical instrument and patient-specific registration jig of FIG. 8 with the patient-specific registration jig being received in the acetabulum of the patient such that the patient-specific surface of the patient-specific registration jig is in contact with the interior surface of the patient's acetabulum.

After the orthopaedic surgeon has secured the patient-specific registration jig 200 to the manual impactor 800, the orthopaedic surgeon may couple the patient-specific registration jig 200 to the acetabulum 400 of the patient by aligning the patient-specific acetabulum registration jig 200 with the patient's acetabulum 400 and moving the patient-specific acetabulum registration jig 200 into contact with the acetabulum 400. Again, because the patient-specific contact surface 106 of the patient-specific acetabulum registration jig 200 is configured to receive a corresponding contour of the patient's acetabulum 400, the patient-specific acetabulum registration jig 200 will seat into, or otherwise couple to, the patient's acetabulum 400 in a singular, unique orientation and location as shown in FIG. 9, with the manual impactor 800 attached. As such, the patient-specific acetabulum registration jig 200 is configured to be inserted or coupled to the patient's acetabulum 400 in a known position relative to the patient's bony anatomy, which facilitates the registration of the manual impactor 800 attached to the patient-specific acetabulum registration jig 200 to the patient's bony anatomy as discussed in more detail below.

Figure 10:
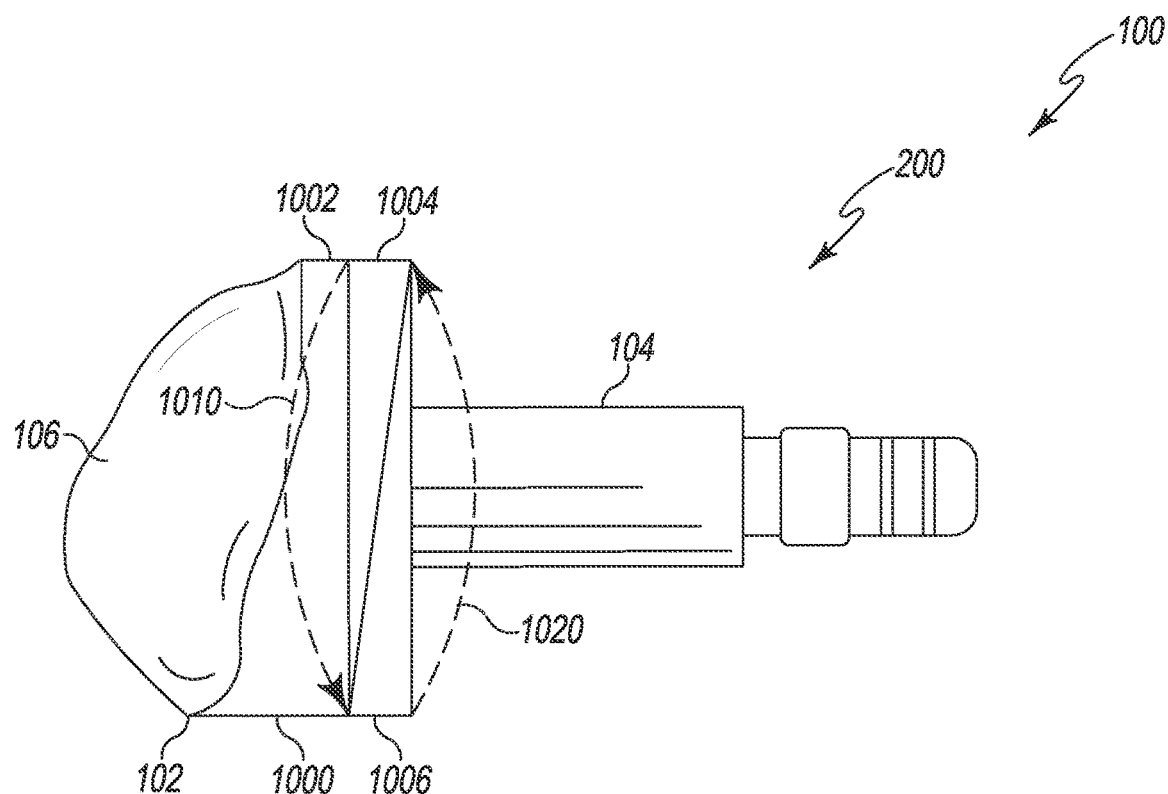
FIG. 10 is an elevation view of another embodiment of the patient-specific registration jig of FIG. 1 embodied as acetabulum registration jig and having movable bases that may be adjusted to modify the inclination and version of an adaptor of the patient-specific registration jig relative to a head of the registration jig.
Figure 11:
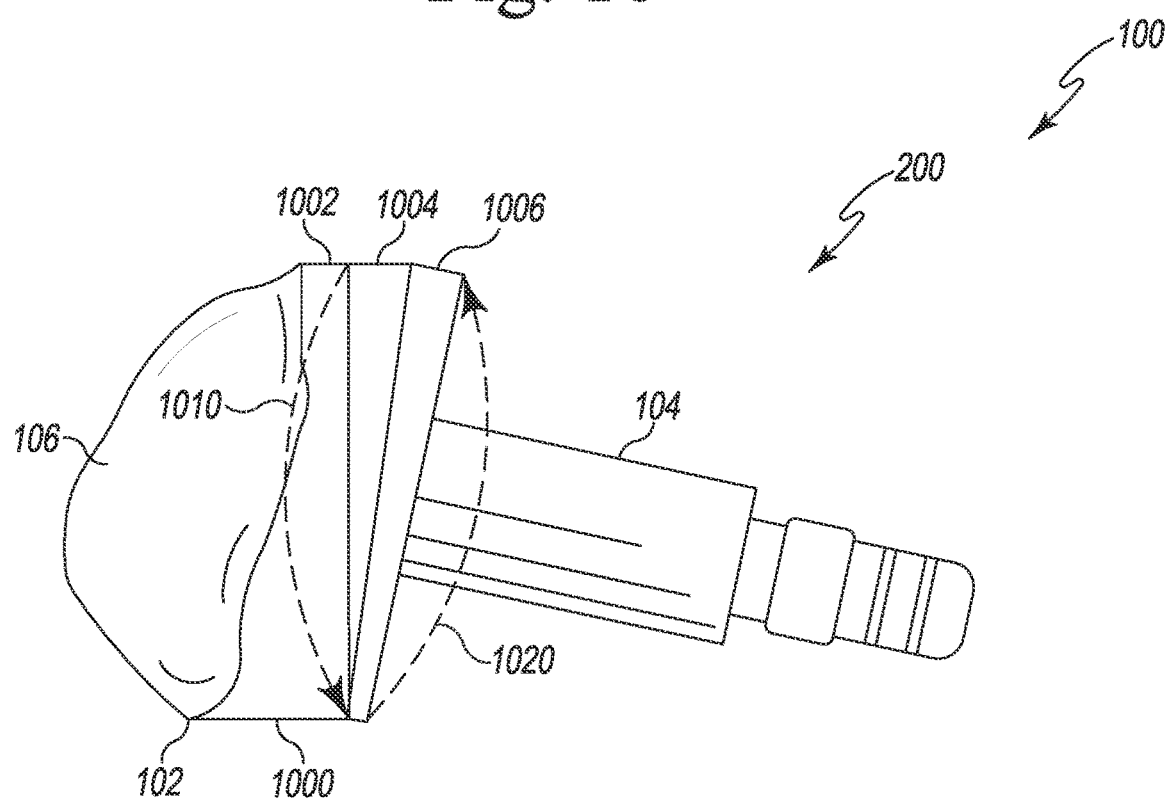
FIG. 11 is an elevation view the patient-specific registration jig of FIG. 10 having one of the bases moved to a different position relative to FIG. 10.

Referring now to FIGS. 10 and 11, in some embodiments, the illustrative patient-specific acetabulum registration jig 200 may include a head 102 having a multi-part base 1000 that is configured to allow the orthopaedic surgeon to modify the inclination and the version of the adaptor 104 of the patient-specific acetabulum registration jig 200 (and, thereby, the inclination and the version of the orthopaedic surgical instrument attached to the jig 200). To do so, some of the parts of the multi-part base 1000 may be moveable relative to each other. For example, in the illustrative embodiment, the multi-part base 1000 includes fixed base 1002, an external base wedge 1006, and an intermediary base wedge 1004 located between the fixed base 1002 and the external base wedge 1006. Each of the base wedges 1004, 1006 are rotatably coupled to the fixed base 1002 such that each of the wedges 1004, 1006 can rotate independently about an axis of rotation defined by the adaptor 104 relative to the fixed base 1002 as shown in FIG. 10 via arrows 1010 and 1020.

Each of the intermediary base wedge 1004 and the external base wedge 1006 has a cylindrical wedge shape. As such, movement of any one or both of the wedges 1004, 1006 causes a repositioning of the adaptor 104 relative to the head 102. For example, by rotating the intermediary base wedge 1004 relative to the external base wedge 1006, the orthopaedic surgeon can adjust or set the inclination of the adaptor 104 relative to the head 102 of the patient-specific acetabulum registration jig 200 (i.e., relative to the patient's acetabulum 400). Similarly, by rotating the external base wedge 1006 relative to the intermediary base wedge 1004, the orthopaedic surgeon can adjust or set the version of the adaptor 104 relative to the head 102 of the patient-specific acetabulum registration jig 200 (i.e., relative to the patient's acetabulum 400). It should be appreciated that because the orthopaedic surgical instrument (e.g., the automated impactor 600 or manual impactor 800) is coupled to the patient-specific acetabulum registration jig 200, the orthopaedic surgeon also adjusts the inclination and version of the orthopaedic surgical instrument relative to the patient's acetabulum 400 via manipulation of the base wedges 1004, 1006. Of course, in other embodiments, the patient-specific acetabulum registration jig 200 may have other adjustment mechanisms for setting the inclination and/or version of the adaptor 104.

Figure 12:
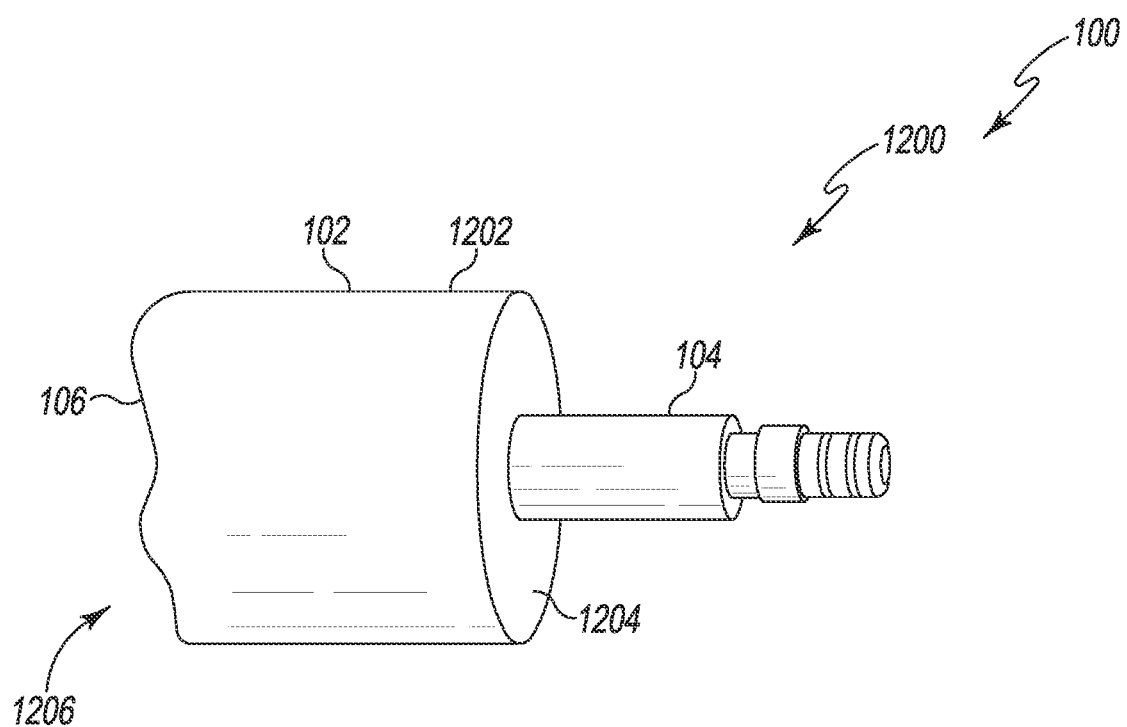
FIG. 12 is an elevation view of another embodiment of the patient-specific registration jig of FIG. 1 embodied as an acetabulum registration jig and having a patient-specific surface configured to contact a rim of the patient's acetabulum.

Referring now to FIG. 12, in another embodiment, the patient-specific registration jig 100 may be embodied as a patient-specific acetabulum registration jig 1200. The patient-specific acetabulum registration jig 1200 is similar to the patient-specific acetabulum registration jig 200 described above, except that the head 102 of the patient-specific acetabulum registration jig 1200 includes a patient-specific contact surface 106 configured to contact the exterior coxal rim of the patient's acetabulum 400. As shown in FIG. 12, the patient-specific acetabulum registration jig 1200 includes the head 102 and the adaptor 104 coupled to the head 102 and extending longitudinally therefrom. The head 102 of the patient-specific acetabulum registration jig 1200 is generally cylindrical in shape and includes a base 1202 having a distal side 1204 and a proximal side 206. The patient-specific contact surface 106 is defined on the proximal side 1206 of the base 1202.

As discussed above, the patient-specific acetabulum registration jig 1200 is configured for use on the rim of the acetabulum 400 of the patient and, as such, the patient-specific contact surface 106 of the patient-specific acetabulum registration jig 200 is configured to contact the bony coxal rim of the patient's acetabulum. Accordingly, the patient-specific contact surface 106 of the patient-specific acetabulum registration jig 1200 includes a negative contour that matches the contour of the patient's acetabulum rim such that the patient-specific acetabulum registration jig 1200 is configured to be coupled to the rim of the patient's acetabulum in a single, unique position (i.e., a unique orientation and location).

It should be appreciated that the head 1202 of the patient-specific acetabulum registration jig 1200 may be hollow on the proximal side 1206 (e.g., similar to a hollow cylinder or tube) and, in such embodiments, only the proximal rim of the head 1202 includes the patient-specific contact surface 106. Alternatively, in some embodiments, the central portion of the proximal side 1206 may be flat or have some other geometry that does not interfere with the coupling of the patient-specific contact surface 106 of the outer rim of the proximal side 1206. In still other embodiments, the central portion of the proximal side 1206 may also include a patient-specific contact surface 106 configured to contact the interior surface of the patient's acetabulum 400 such that the illustrative patient-specific acetabulum registration jig 1200 contact both the patient's acetabulum 400 and the coxal rim of the patient's acetabulum 400.

Figure 13:
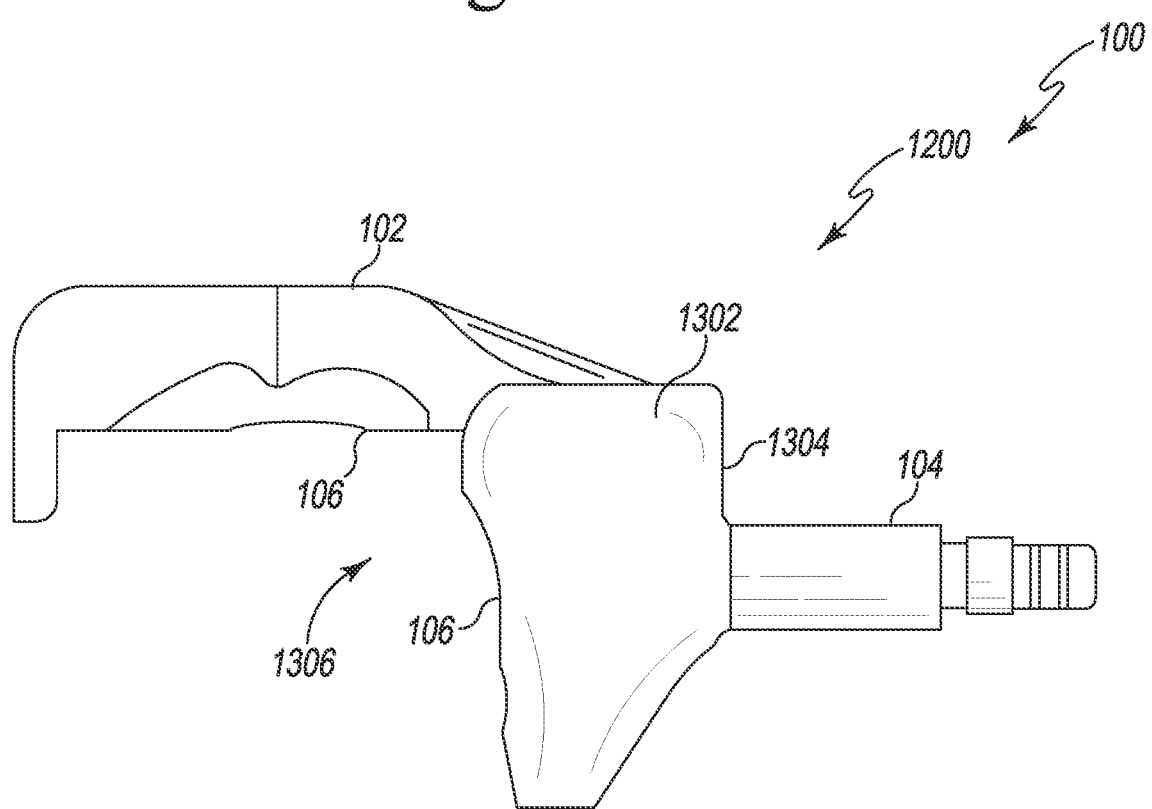
FIG. 13 is an elevation view of another embodiment of the patient-specific registration jig of FIG. 1 embodied as a femoral registration jig and having a patient-specific surface configured to contact a bony surface of the patient's femur.

Referring now to FIG. 13, in another embodiment, the patient-specific registration jig 100 may be embodied as a patient-specific femoral registration jig 1300. The illustrative patient-specific femoral registration jig 1300 includes a head 102 and an adaptor 104 coupled to the head 102 and extending longitudinally therefrom. However, the head 102 of the patient-specific femoral registration jig 1300 is shaped and configured to couple to a distal end of a patient's femur. The head 102 of the patient-specific femoral registration jig 1300 includes a base 1302 having a distal side 1304 and a proximal side 1306. The patient-specific contact surface 106 is defined on the proximal side 1306 of the base 1302. The patient-specific femoral registration jig 1300 is configured for use on a femur of the patient and, as such, the patient-specific contact surface 106 of the patient-specific femoral registration jig 1300 is configured to contact the bony surface of the patient's femur. In particular, the patient-specific contact surface 106 of the patient-specific femoral registration jig 1300 includes a negative contour that matches the contour of a portion of the greater trochanter of the patient's femur such that the patient-specific femoral registration jig 1300 is configured to receive, or otherwise be coupled to, the patient's distal femur in a single, unique position (i.e., a unique orientation and location). As such, the patient-specific femoral registration jig 1300 may be used to register an orthopaedic surgical instrument to the bony anatomy of the patient using the patient's femur in a manner similar to the patient-specific acetabulum registration jigs 200, 1200 discussed above.

Figure 14:
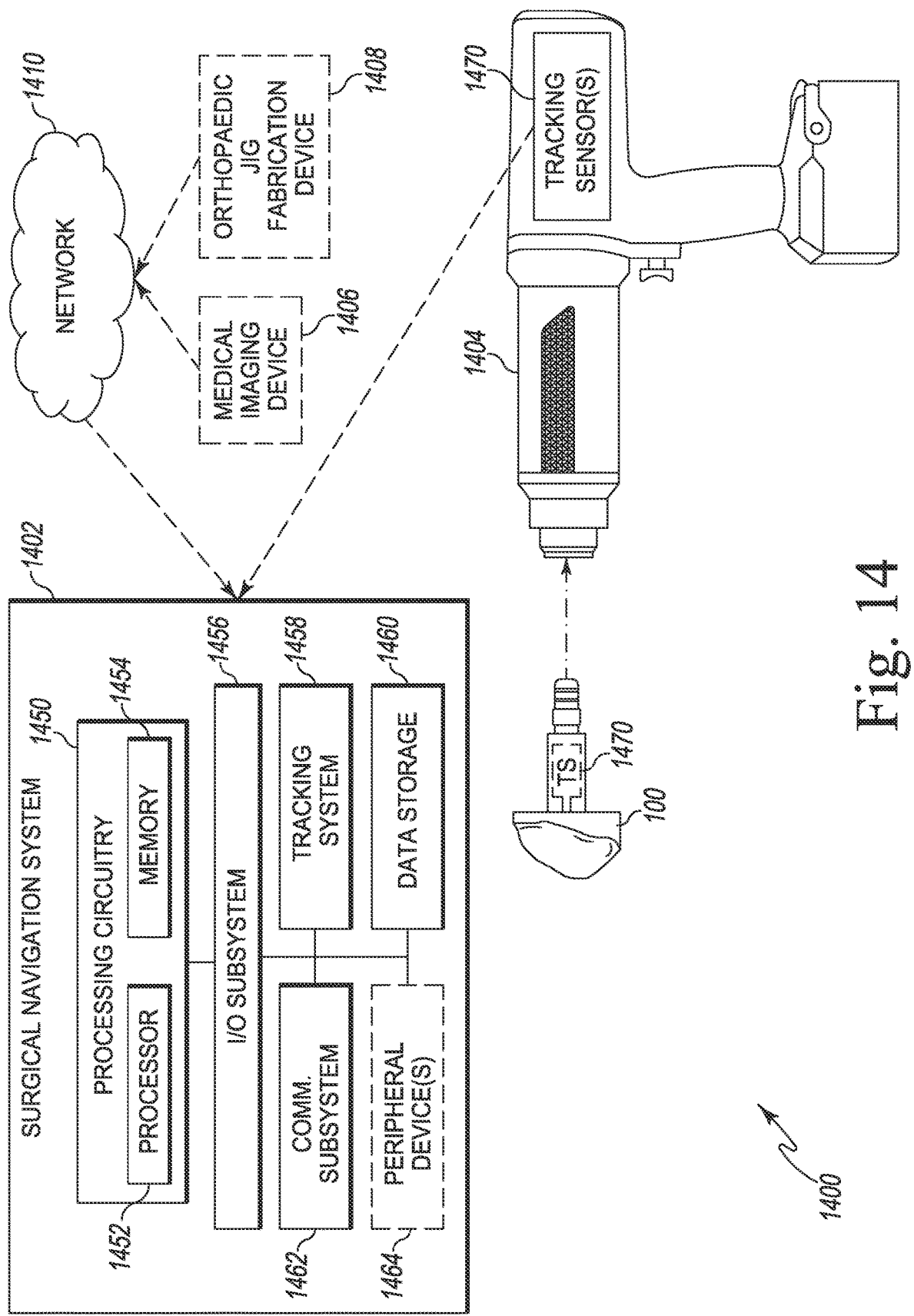
FIG. 14 is a simplified block diagram of at least one embodiment of a system for registering and tracking an orthopaedic surgical instrument.

Referring now to FIG. 14, a system 1400 for registering and tracking an orthopaedic surgical instrument 1404 includes a surgical navigation system 1402, the orthopaedic surgical instrument 1404, and the patient-specific registration jig 100. Additionally, in some embodiments as discussed below, the system 1400 may also include a medical imaging device 1406 and/or a registration jig fabrication device 1408, each of which may be communicatively coupled to the surgical navigation system 1402 over a network 1410.

In use, as discussed in more detail below, an orthopaedic surgeon may operate the surgical navigation system 1402 to register the orthopaedic surgical instrument 1404 to the patient's bony anatomy using the patient-specific registration jig 100 and subsequently track the positioning of the orthopaedic surgical instrument 1404 relative to the patient's bony anatomy. To do so, the orthopaedic surgeon assembles the patient-specific registration jig 100 and the orthopaedic surgical instrument 1404. For example, the orthopaedic surgeon may insert the adaptor 104 of the patient-specific registration jig 100 into a clutch of the orthopaedic surgical instrument 1404. Once assembled, the orthopaedic surgeon couples the patient-specific registration jig 100 to the patient's bony anatomy. For example, the orthopaedic surgeon may insert the patient-specific registration jig 100 into the patient's acetabulum or attach the patient-specific registration jig 100 to the patient's femur or other bone depending on the particular orthopaedic surgery being performed. As discussed above, because the patient-specific registration jig 100 includes the patient-specific contact surface 106, the patient-specific registration jig 100 is configured to couple to the relevant portion of the patient's bony anatomy in a unique position (e.g., a unique orientation and location).

After the orthopaedic surgeon has coupled the patient-specific registration jig 100 to the patient's bony anatomy, the orthopaedic surgeon may operate the surgical navigation system 1402 to register the orthopaedic surgical instrument 1404 to the patient's bony anatomy. In doing so, the surgical navigation system may generate registration data indicative of the position of the orthopaedic surgical instrument 1404 in three-dimensional space relative to the patient's bony anatomy. Once so registered, the orthopaedic surgeon may then utilize the surgical navigation system to track the position of the orthopaedic surgical instrument 1404, relative to the patient's bony anatomy, during use of the orthopaedic surgical instrument 1404 (e.g., to impact an orthopaedic prosthesis into the patient's bony anatomy). As discussed above, by tracking the position of the orthopedic surgical instrument 1404, the orthopaedic surgeon also tracks the position of any orthopaedic prosthesis attached to the registered orthopaedic surgical instrument 1404 (e.g., an acetabular implant attached to a registered impactor). As such, the orthopaedic surgeon may use the registered orthopaedic surgical instrument 1404 to track and validate the implanted location and orientation of the associated orthopaedic prosthesis.

Additionally, in some embodiments, the orthopaedic surgeon may utilize the system 1400 to fabricate the patient-specific registration jig 100. To do so, the orthopaedic surgeon may obtain medical images of the patient's relevant bony anatomy (e.g., of the patient's hip joint and/or femur) from the medical imaging device 1406. The surgical navigation system 1402, the registration jig fabrication device 1408, and/or other compute device may generate a three-dimensional model of the patient-specific registration jig 100 based on the medical images. In doing so, the patient-specific contact surface 106 of the model of the patient-specific registration jig 100 is designed based on the medical images of the patient's bony anatomy. The model of the patient-specific registration jig 100 is provided to (or generated by) the orthopaedic jig fabrication device 1408, which fabricates the patient-specific registration jig 100 based on the three-dimensional model. For example, the registration jig fabrication device 1408 may machine or 3D print the patient-specific registration jig 100.

The surgical navigation system 1402 may be embodied as any type of computer or computation device capable of performing the functions described herein. For example, the surgical navigation system 1402 may be embodied as an operating room computer, a server, a desktop computer, a laptop computer, a tablet computer, a smartphone, a mobile computer, a smart device, a wearable computer system, or other computer or computer device. As shown in FIG. 14, the illustrative surgical navigation system 1402 includes an processing circuitry 450, an input/output ("I/O") subsystem 1456, a tracking subsystem 1458, a data storage 1460, a communication subsystem 1462 and, in some embodiments, one or more peripheral devices 1464. Of course, the surgical navigation system 1402 may include additional or other components, such as those commonly found in a typical computer device or surgical navigation computer (e.g., a display, speakers, touchscreen, etc.), in other embodiments. Additionally, in some embodiments, one or more of the illustrative components may be incorporated in, or otherwise form a portion of, another component.

The processing circuitry 1450 may be embodied as any type of controller, functional block, digital logic, or other component, device, circuitry, or collection thereof capable of performing the functions described herein. In illustrative embodiment, the processing circuitry 1450 includes a processor 1452 and a memory 1454. The processor 1452 may be embodied as any type of processor capable of performing the functions described herein. For example, the processor 1452 may be embodied as a single or multi-core processor(s), digital signal processor, microcontroller, or other processor or processing/controlling circuit. Similarly, the memory 1454 may be embodied as any type of volatile and/or non-volatile memory or data storage capable of performing the functions described herein. In operation, the memory 1454 may store various data and software used during operation of the surgical navigation system 1402 such as operating systems, applications, executable software, programs, libraries, and drivers, which may be executed or otherwise used by the processor 1452.

The processing circuitry 1450 is communicatively coupled to other components of the surgical navigation system 1402 via the I/O subsystem 1456, which may be embodied as circuitry and/or components to facilitate input/output operations between the processing circuitry 1450 (e.g., the processor 1452 and the memory 1454) and the other components of the surgical navigation system 1402. For example, the I/O subsystem 1456 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 1456 may form a portion of a system-on-a-chip (SoC) and be incorporated, along with the processing circuitry 1450 (e.g., the processor 1452 and the memory 1454) and other components of the processing circuitry 1450, on a single integrated circuit chip. Additionally, in some embodiments, the memory 1454, or portions of the memory 1454, may be incorporated into the processor processing circuitry 1450.

The tracking subsystem 1458 may be embodied as any number and type of electronic components, devices, and/or associated software capable of tracking the position of the orthopaedic surgical instrument 1404 in the operative theater. To do so, the tracking subsystem 1458 may utilize any suitable tracking technology and/or algorithm (e.g., a triangulation, trilateration, optical, etc.). For example, the tracking subsystem 1458 may be embodied as an electrical tracking subsystem in which the position of the orthopaedic surgical instrument 1404 is based on communications received from one or more wireless tracking sensors included in the orthopaedic surgical instrument 1404. Alternatively, in other embodiments, the tracking subsystem 1458 may be embodied as an optical tracking subsystem in which the position of the orthopaedic surgical instrument 1404 is based on the relative location of optical sensors attached to the orthopaedic surgical instrument 1404. Regardless, the tracking subsystem 1458 is configured to determine the relative position (location and/or orientation) of the orthopaedic surgical instrument 1404 relative to the patient's bony anatomy (e.g., in a coordinate system defined by the patient's bony anatomy).

The data storage 1460 may be embodied as any type of device or devices configured for short-term and/or long-term storage of data such as, for example, solid-state drives, hard disk drives, memory devices and circuits, memory cards, non-volatile flash memory, or other data storage devices. In the illustrative embodiment, the data storage 1460 stores various data used by the surgical navigation system to perform the functions described herein. For example, the data storage 1460 may store one or more medical images of the patient's bony anatomy [produced by the medical imaging device 1406, the three-dimensional model of the patient-specific registration jig 100, the registration data produced during registration of the orthopaedic surgical instrument 1404, and/or other data.

The communication subsystem 1462 may be embodied as any type of communication circuit, device, or collection thereof, capable of enabling communications between the surgical navigation system 1402, the medical imaging device 1406, the orthopaedic jig fabrication device 1408, and/or other devices of the system 1400. To do so, the communication subsystem 1462 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

The one or more peripheral device(s) 1464 may include any number of additional peripheral or interface devices (e.g., touchscreen, keyboard, mouse, etc.), such as other input/output devices (e.g., displays), storage devices, and so forth. The particular devices included in the peripheral device(s) 1464 may depend on, for example, the type and/or intended use of the surgical navigation system 1402.

The orthopaedic surgical instrument 1404 may be embodied as any type of orthopaedic surgical instrument or tool capable of being coupled to the patient-specific registration jig 100 and tracked by the surgical navigation system 1402. For example, the orthopaedic surgical instrument 1404 may be embodied as a manual or automated impactor in the illustrative embodiment.

The orthopaedic surgical instrument 1404 includes one or more tracking sensors 1470. The tracking sensors 1470 may be embodied as any type of tracking sensors 1470 usable by the tracking subsystem 1458 of the surgical navigation system 1402 to determine a present position of the orthopaedic surgical instrument 1404. For example, the tracking sensors 1470 may be embodied as one or more wireless sensors configured to transmit data (e.g., a beacon) to the tracking subsystem 1458, which may determine the position of the orthopaedic surgical instrument 1404 based on the received signals (e.g., via triangulation or trilateration). Alternatively, in other embodiments, the tracking sensors 1470 may be embodied as one or more optical tracking sensors, which are usable by a camera system of the tracking subsystem 1458 to determine the position of the orthopaedic surgical instrument 1404. Additionally, in some embodiments, one or more tracking sensors 1470 may, alternatively or additionally, be included in the patient-specific registration jig 100 as shown in dashed line in FIG. 14.

The medical imaging device 1406 may be embodied as any type of device or collection of devices capable of pre-operatively and/or intra-operatively generating medical images of the bony anatomy of the patient. For example, the medical imaging device 1406 may be embodied as an X-Ray imaging machine or other medical imagining device capable of generating two-dimensional medical images. Alternatively, in other embodiments, the medical imaging device 1406 may be embodied an imaging device capable of generating three-dimensional medical images, such as an MRI.

The orthopaedic jig fabrication device 1408 may be embodied as any type of manufacturing device or collection of devices capable of producing the patient-specific registration jig 100. For example, the orthopaedic jig fabrication device 1408 may be embodied as a machining device capable of machining the patient-specific registration jig 100, a 3D printing device capable of fabricating the patient-specific registration jig 100, and/or other manufacturing device. In some embodiments, the speed at which the orthopaedic jig fabrication device 1408 can produce the patient-specific registration jig 100 may be a consideration for the selection of that device 1408.

The network 1410 may be embodied as any type of communication network capable of facilitating communication between the surgical navigation system 1402, the medical imaging device 1406, the orthopaedic jig fabrication device 1408, and/or other components of the system 1400. As such, the network 1410 may include one or more networks, routers, switches, gateways, computers, and/or other intervening devices. For example, the network 1410 may be embodied as or otherwise include one or more local or wide area networks, cellular networks, publicly available global networks (e.g., the Internet), an ad hoc network, a short-range communication network or link, or any combination thereof.

Figure 15A:
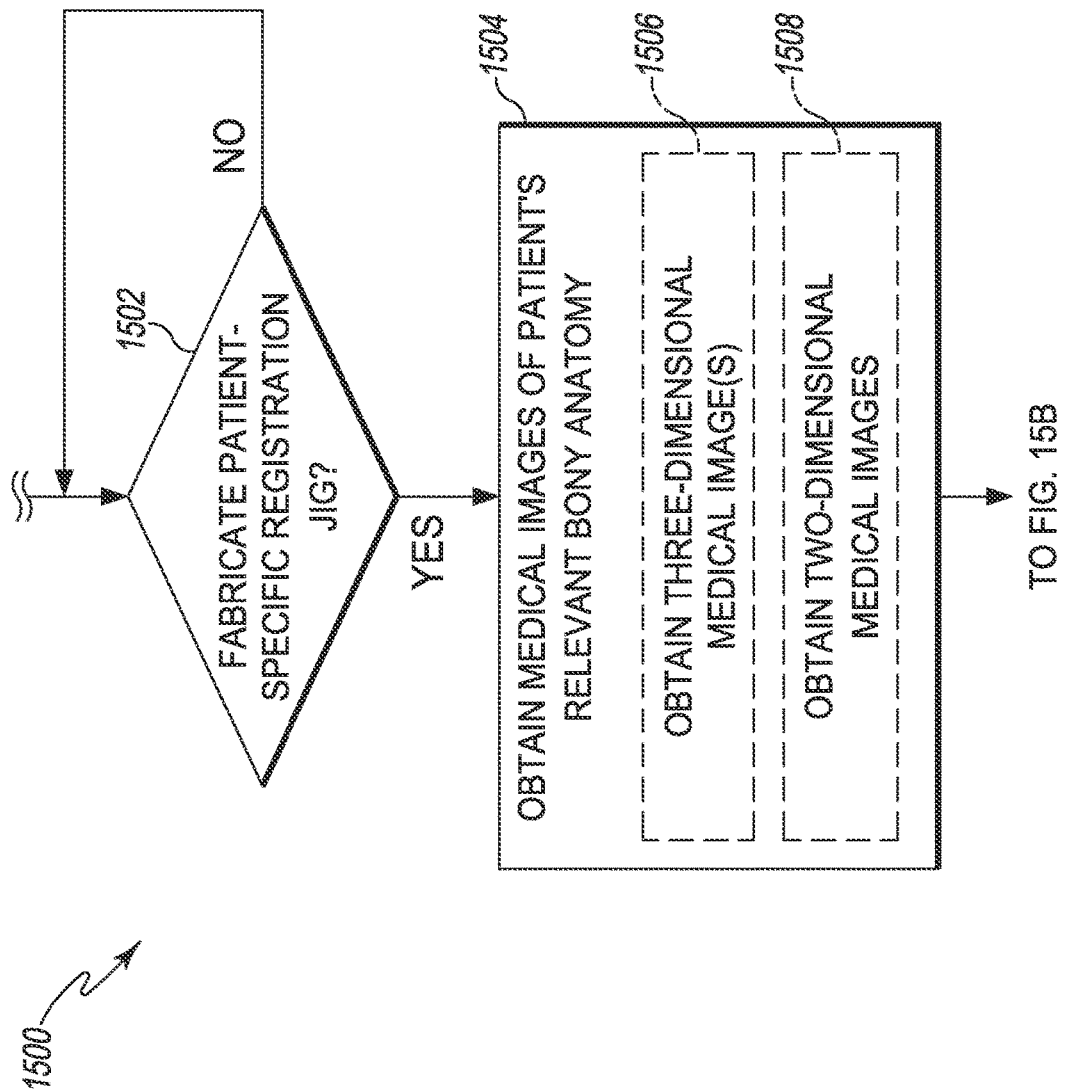
FIGS. 15A-15C are a simplified flow diagram of at least one embodiment of a method for fabricating a patient-specific registration jig.
Figure 15B:
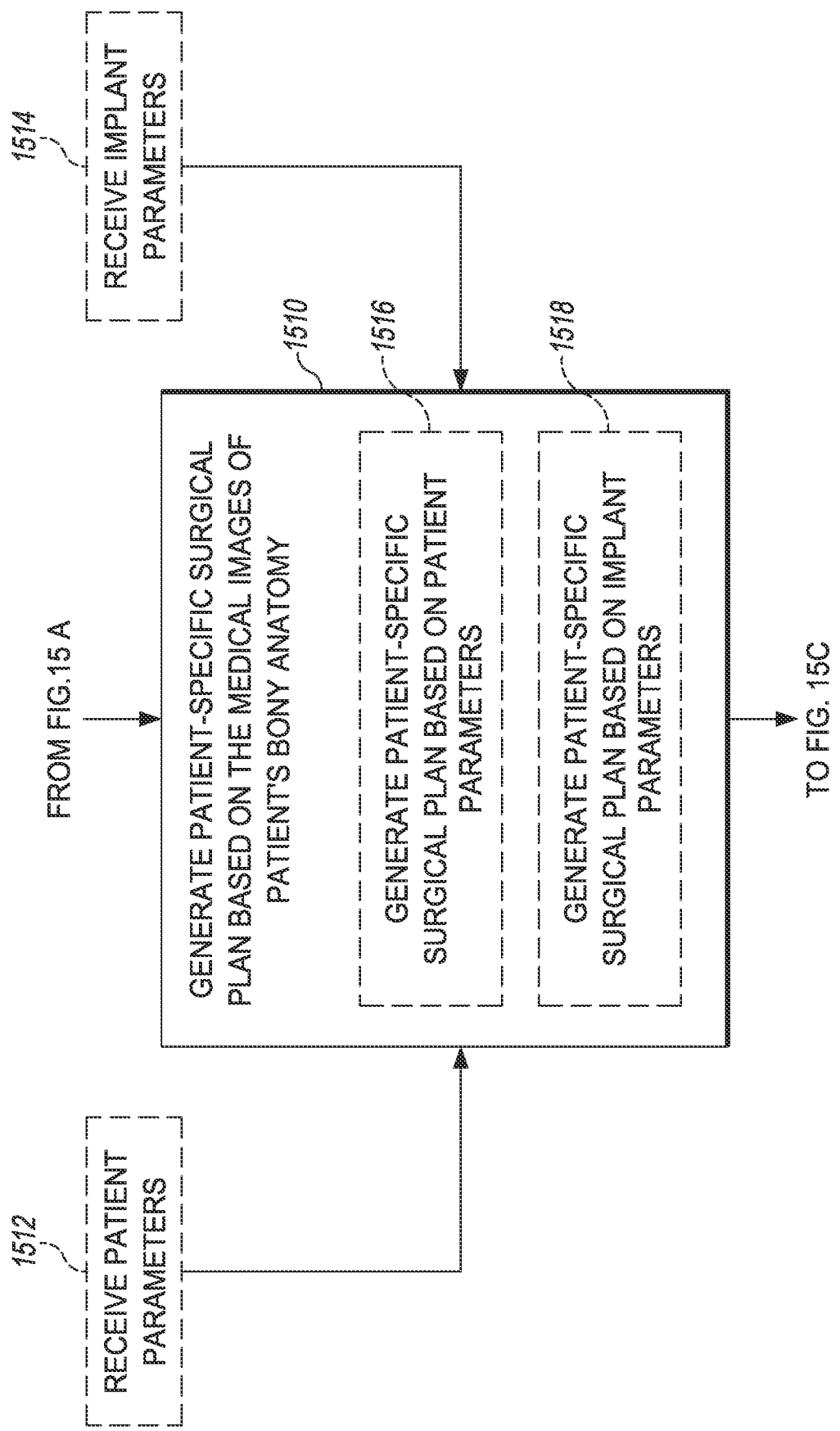
Figure 15C:
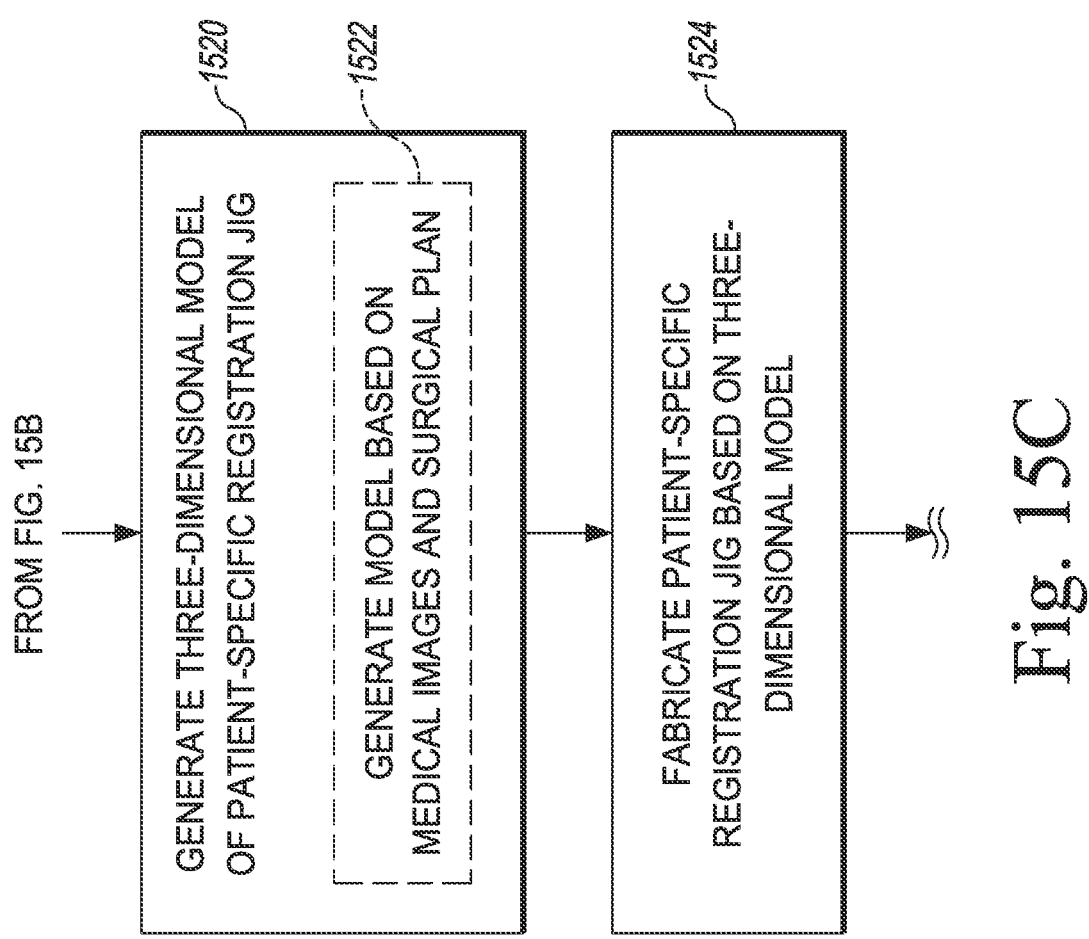

Referring now to FIGS. 15A-15C, in use, the surgical navigation system 1402 (and/or other components of the system 1400) may perform a method 1500 for fabricating the patient-specific registration jig 100. The method 1500 begins with block 1502 in which the surgical navigation system 1402 determines whether a patient-specific registration jig 100 is to be produced. If so, the method 1500 advances to block 1504.

In block 1504, the surgical navigation system 1402 obtains medical images of the patient's relevant bony anatomy (e.g., of the patient's acetabulum, femur, etc.). To do so, in some embodiments, the medical imaging device 1406 may generate the medical images and transfer those images to the surgical navigation system 1402. In other embodiments, the surgical navigation system 1402 may produce the medical images itself or otherwise receive the medical images from another device. In some embodiments, as shown in block 1506, the surgical navigation system 1402 may obtain three-dimensional medical images of the patient's relevant bony anatomy (e.g., in those embodiments in which the medical imaging device 1406 is an MRI device). In other embodiments, as shown in block 1508, the surgical navigation system 1402 may obtain two-dimensional medical images of the patient's relevant bony anatomy (e.g., in those embodiments in which the medical imaging device 1406 is an X-Ray device). In such embodiments, the medical imaging device 1406 or the surgical navigation system 1402 may be configured to convert the two-dimensional medical images into a three-dimensional medical image using a 2D-3D conversion algorithm.

In block 1510, the orthopaedic surgeon may utilize the surgical navigation system 1402 or other computer device to generate a patient-specific surgical plan based on the medical images of the patient's relevant bony anatomy. The patient-specific surgical plan may be developed based on a number of various criteria such as the orthopaedic implant to be used, characteristics of the patient, the preferences of the orthopaedic surgeon, the type of orthopaedic surgical procedure or approach to be used, and so forth.

For example, in block 1512, the surgical navigation system 1402 may receive patient parameters. The patient parameters may include any information related to the patient that may be useful in designing the patient-specific surgical plan (e.g., the patient's age, gender, activity level, flexibility, medical history, etc.). The patient parameters may be supplied by the orthopaedic surgeon or otherwise obtained by the surgical navigation system 1402 from another compute system (e.g., from a medical records system). In such embodiments, the surgical navigation system 1402 may generate the patient-specific surgical plan in block 1516 based on the patient parameters received in block 1512.

Additionally, in block 1514, the surgical navigation system 1402 may receive implant parameters. The implant parameters may include any information related to the orthopaedic prosthesis to be implanted into the patient (e.g., the type, size, etc.) The implant parameters may be supplied by the orthopaedic surgeon or otherwise obtained by the surgical navigation system 1402 from another compute system. In such embodiments, the surgical navigation system 1402 may generate the patient-specific surgical plan in block 1518 based on the implant parameters received in block 1514.

Subsequently, in block 1520, the surgical navigation system 1402 generates a three-dimensional model of the patient-specific registration jig 100. To do so, the surgical navigation system 1402 may generate the three-dimensional model of the patient-specific registration jig in block 1522 based on the medical images of the patient's relevant bony anatomy obtained in block 1504 and/or the surgical plan generated in block 1510. For example, the surgical navigation system 1402 may design the patient-specific contact surface 106 of the patient-specific registration jig based on the contour of the relevant bony anatomy of the patient as shown in the medical images. Although described as being performed by the surgical navigation system 1402, the three-dimensional model of the patient-specific registration jig 100 may be generated by other devices of the system 1400 in other embodiments. For example, the medical imaging device 1406 or the orthopaedic jig fabrication device 1408 may generate the three-dimensional model of the patient-specific registration jig 100 in some embodiments.

In block 1524, the surgical navigation system 1402 fabricates the patient-specific registration jig 100 based on the three-dimensional model of the patient-specific registration jig 100. To do so, in the illustrative embodiment, the surgical navigation system 1402 transmits the three-dimensional model to the orthopaedic jig fabrication device 1408, which fabricates the patient-specific registration jig 100. To do so, the orthopaedic jig fabrication device 1408 may use any suitable manufacturing technique such as a milling process, a 3D printing process, and so forth. It should be appreciated that, in some embodiments, the orthopaedic jig fabrication device 1408 may form a part of the surgical navigation system 1402 and/or be co-located with the surgical navigation system 1402 to increase the speed at which the patient-specific registration jig 100 is fabricated and subsequently used in a corresponding orthopaedic surgical procedure.

Figure 16A:
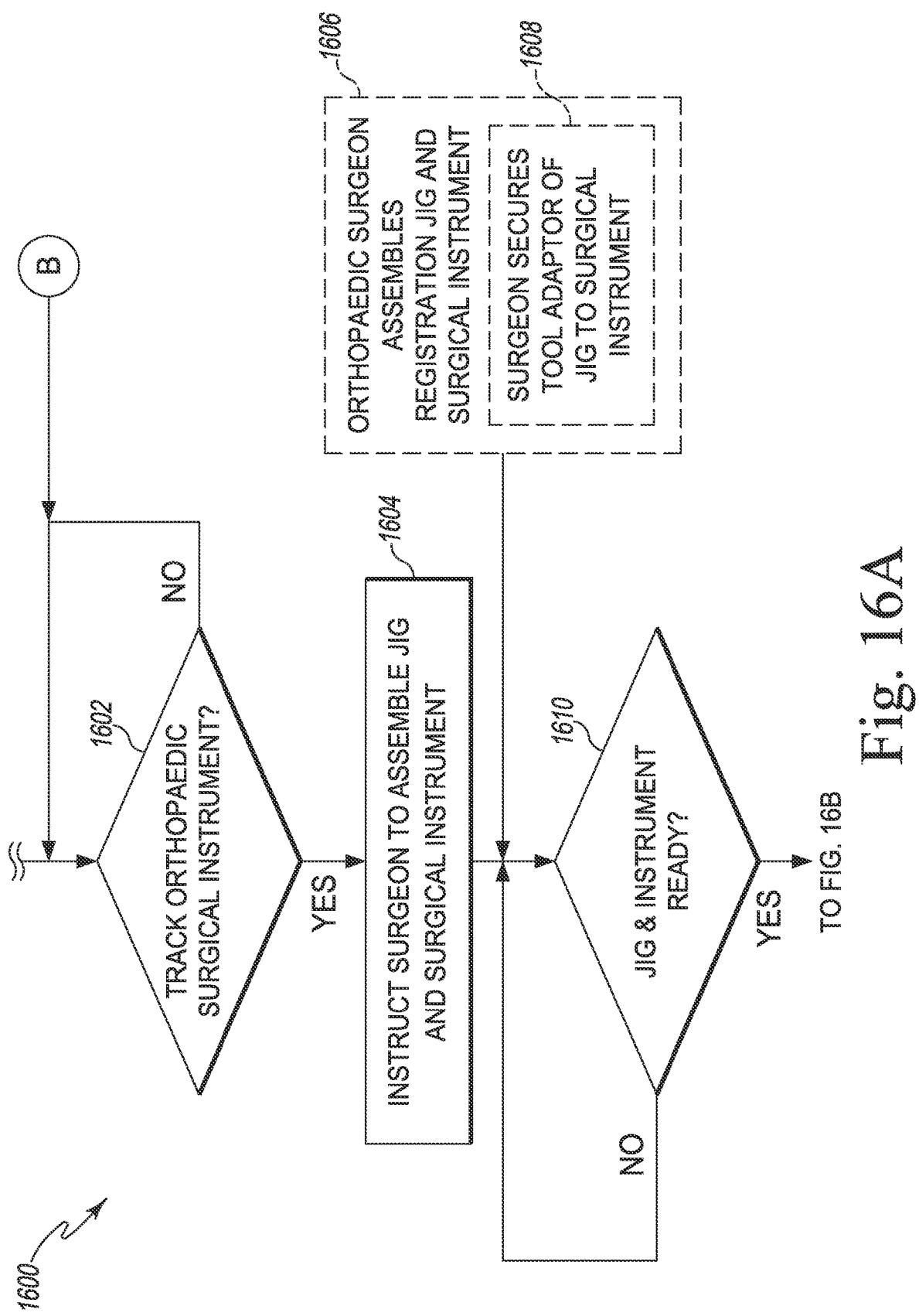
FIGS. 16A-16C are a simplified flow diagram of at least one embodiment of a method for registering and tracking an orthopaedic surgical instrument using the patient-specific registration jig of FIG. 1.
Figure 16B:
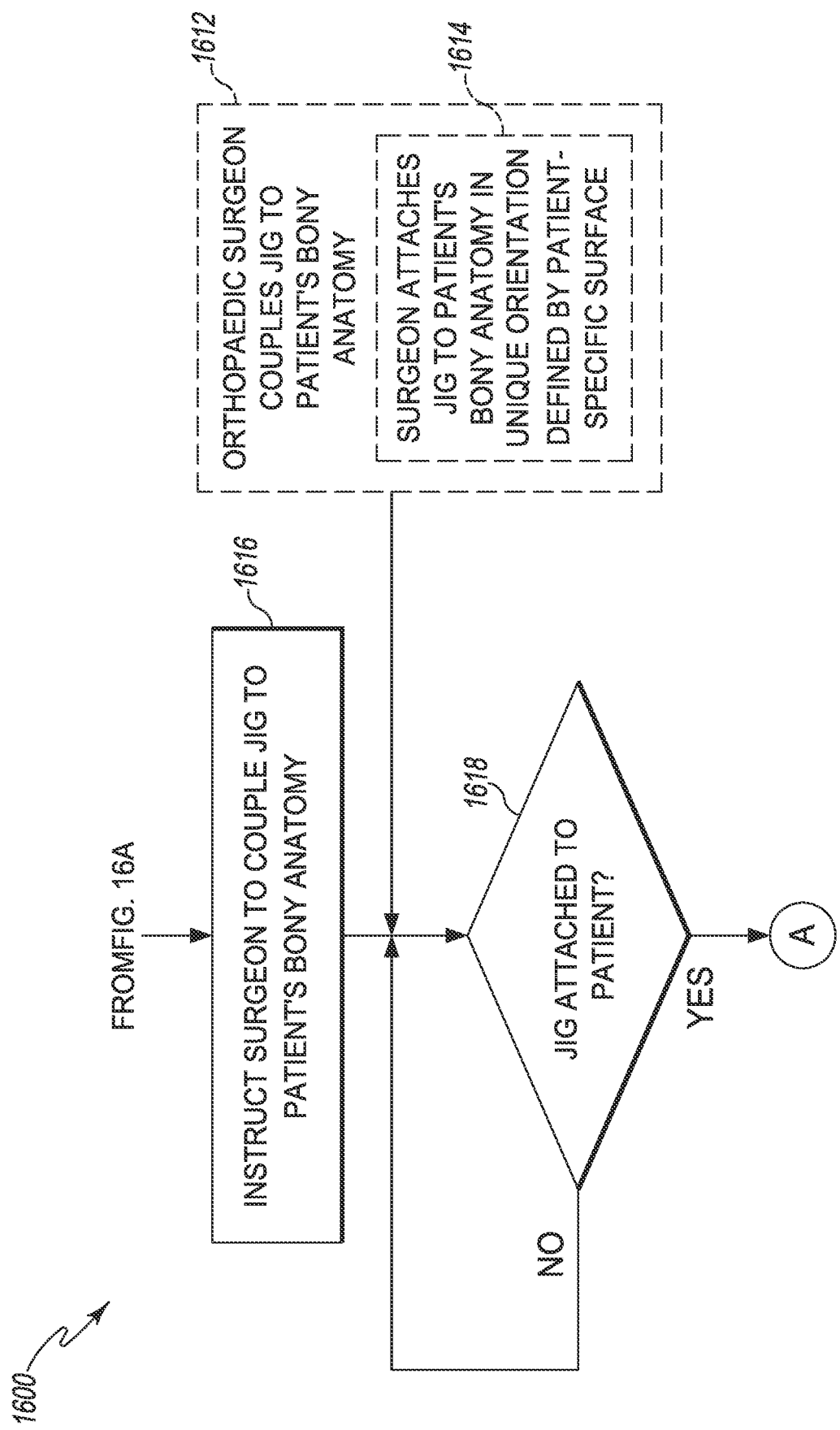
Figure 16C:
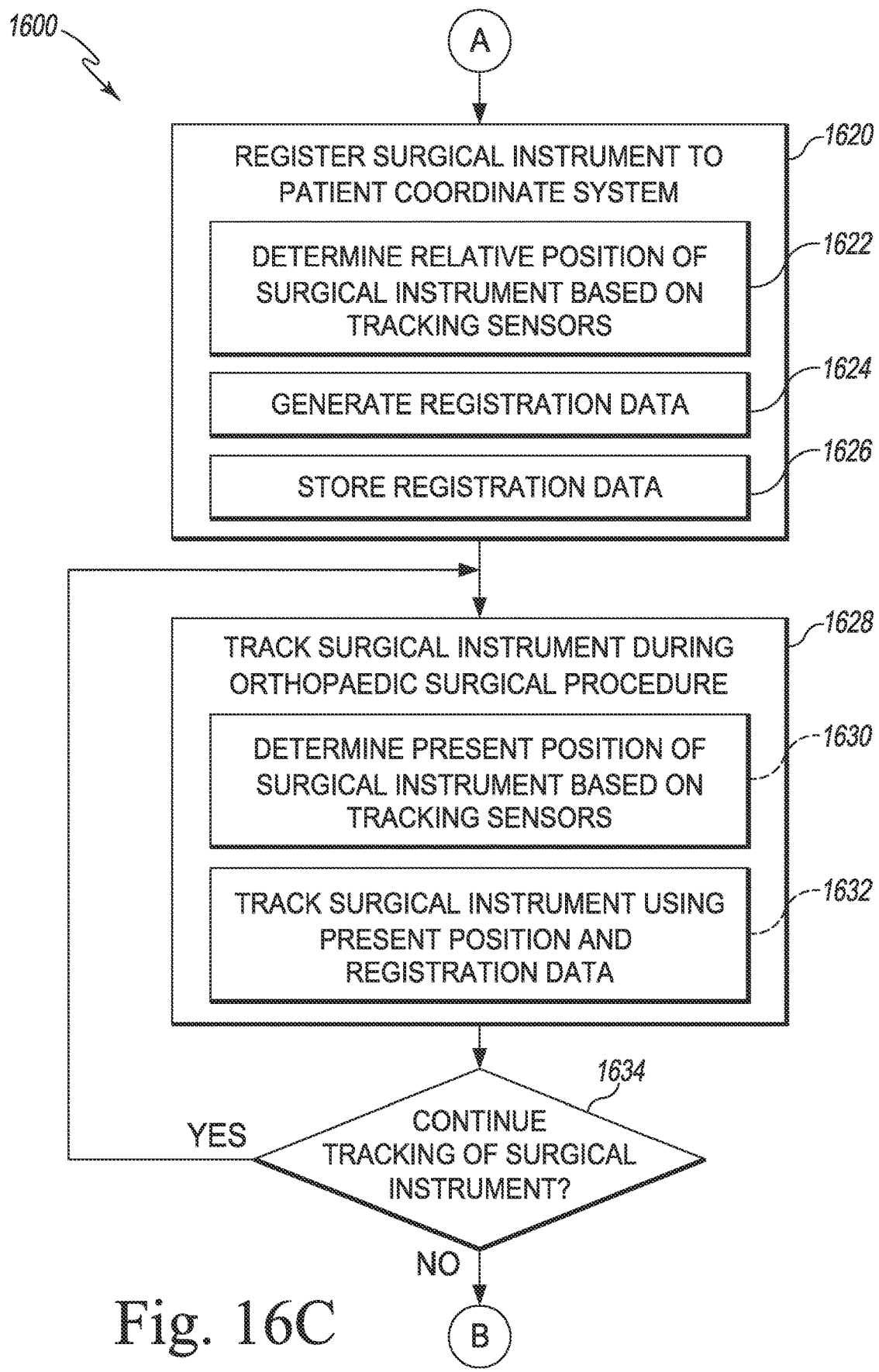

Referring now to FIGS. 16A-16C, in operation, the surgical navigation system 1402 may perform a method 1600 for registering and tracking the orthopaedic surgical instrument 1404 in a surgical environment. It should be appreciated that some of the blocks of method 1600 may be performed by the orthopaedic surgeon or other healthcare provider and are illustrated in FIGS. 16A-16C as dashed block.

The method 1600 begins with block 1602 in which the surgical navigation system 1402 determines whether the orthopaedic surgeon desires to track the orthopaedic surgical instrument 1404. If so, the method 1600 advances to block 1604 in which the surgical navigation system 1402 instructs the orthopaedic surgeon to assemble the patient-specific registration jig 100 and the orthopaedic surgical instrument 1404 to be tracked. In block 1606, the orthopaedic surgeon assembles the patient-specific registration jig 100 and the orthopaedic surgical instrument 1404. To do so, for example, the orthopaedic surgeon may secure the adaptor 104 of the patient-specific registration jig 100 to a clutch of the orthopaedic surgical instrument 1404 in block 1608, as discussed above.

After the orthopaedic surgeon has assembled the patient-specific registration jig 100 and the orthopaedic surgical instrument 1404, the surgical navigation system 1402 confirms that the assembled patient-specific registration jig 100 and the orthopaedic surgical instrument 1404 are ready for use in block 1610. For example, the surgical navigation system 1402 may prompt the orthopaedic surgeon for a confirmatory input.

If so, the method 1600 advances to block 1616 in which the surgical navigation system 1402 instructs the orthopaedic surgeon to couple the patient-specific registration jig 100 to the patient's bony anatomy. In response, in block 1612, the orthopaedic surgeon couples the patient-specific registration jig 100, with the orthopaedic surgical instrument 1404 attached thereto, to the relevant portion of the patient's bony anatomy. In doing so, in block 1614, the orthopaedic surgeon couples the patient-specific registration jig 100 in a unique position (e.g., location and/or orientation) on the relevant portion of the patient's bony anatomy, which is defined by the patient-specific contact surface 106 of the patient-specific registration jig 100 as discussed above. For example, the orthopaedic surgeon may insert, or otherwise contact, the head 102 of the patient-specific registration jig 100 into the acetabulum 400 of the patient as shown and described above in regard to FIG. 7.

After the orthopaedic surgeon has coupled the patient-specific registration jig 100 to the patient's bony anatomy, the surgical navigation system 1402 confirms that the assembled patient-specific registration jig 100 has been coupled to the relevant portion of the patient's bony anatomy in block 1618. For example, the surgical navigation system 1402 may prompt the orthopaedic surgeon for a confirmatory input.

If so, the method 1600 advances to block 1620 of FIG. 16C in which the surgical navigation system 1402 registers the orthopaedic surgical instrument 1404 to the bony anatomy of the patient (e.g., to a coordinate system defined by the bony anatomy of the patient). To do so, in some embodiments in block 1622, the surgical navigation system 1402 may determine the relative position (e.g., location and/or orientation) of the orthopaedic surgical instrument 1404 while the patient-specific registration jig 100 (and the attached orthopaedic surgical instrument 1404) is coupled to the patient's bony anatomy based on the tracking sensors 1470. For example, in some embodiments, the surgical navigation system 1402 is configured to receive wireless communications and/or data from the tracking sensors 1470 from which the surgical navigation system 1402 can determine the location and/or orientation of the orthopaedic surgical instrument 1404. Alternatively, in other embodiments, the surgical navigation system 1402 may utilize an optical tracking system (e.g., a camera and optical tracking sensors 1470) to determine the relative position of the orthopaedic surgical instrument 1404.

In block 1624, the surgical navigation system 1402 may generate registration data based on the determined position of the orthopaedic surgical instrument 1404. For example, the registration data may be indicative of the position of the orthopaedic surgical instrument 1404 relative to the patient's bony anatomy when the patient-specific registration jig 100 is coupled thereto. In this way, the registration data may define conversion data usable to convert a determined position of the orthopaedic surgical instrument 1404 in three-dimensional space to a location of position in the patient coordinate system. In some embodiments, in block 1626, the surgical navigation system 1402 may store the generated registration data. For example, the surgical navigation system 1402 may store the registration data in the data storage 1460.

After the orthopaedic surgical instrument 1404 has been registered to the patient's bony anatomy, the method 1600 advances to block 1628 in which the surgical navigation system 1402 may track the orthopaedic surgical instrument 1404 during the performance of a related orthopaedic surgical procedure. To do so, in block 1630, the surgical navigation system 1402 may determine the present position of the orthopaedic surgical instrument 1404 using the tracking subsystem 1458 and the tracking sensor(s) 1470 as discussed above. In block 1632, the surgical navigation system 1402 may track the position of the orthopaedic surgical instrument 1404 using the present position determined in block 1630 and the registration data generated in block 1624. For example, the surgical navigation system 1402 may determine a present position of the orthopaedic surgical instrument 1404 in a coordinate system defined by the patient's bony anatomy based on the registration data and the presently determined position of the orthopaedic surgical instrument 1404. In some embodiments, the surgical navigation system 1402 may provide a visual indication of such tracking and position determination to the orthopaedic surgeon and/or provide other surgical navigation services. Again, as discussed above, it should be appreciated that the tracking of the registered orthopaedic surgical instrument 1404 also allows the orthopaedic surgeon to verify that any final implant is properly positioned relative to the patient's bony anatomy via the tracked location and orientation of the orthopaedic surgical instrument 1404.

In block 1634, the surgical navigation system 1402 determines whether to continue tracking the orthopaedic surgical instrument 1404. If so, the method 1600 loops back to block 1628 in which the surgical navigation system 1402 continues to determine the position of the orthopaedic surgical instrument 1404 relative to the patient's bony anatomy. If not, the method 1600 loops back to block 1602 in which the surgical navigation system 1402 determines whether to track another orthopaedic surgical instrument.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and/or systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. A patient-specific registration jig for registering an orthopaedic surgical instrument with a bony anatomy of a patient, the patient-specific registration jig comprising:
    a head having a patient-specific contact surface configured to contact a portion of the patient's bony anatomy and a multi-part base, wherein the patient-specific contact surface includes a patient-specific negative contour configured to receive a portion of the patient's bony anatomy; and
    an adaptor coupled to the multi-part base of the head and extending longitudinally therefrom, wherein the adaptor includes (i) an elongated shank having a first end coupled to the head and a second end and (ii) an adaptor end attached to the second end of the elongated shank and configured to be received by a clutch of the orthopaedic surgical instrument,
    wherein the multi-part base is adjustable to modify an inclination angle or a version angle of the head relative to the adaptor and comprises a fixed base connected to the head, a first movable wedge, and a second movable wedge interposed between the fixed base and the first movable wedge,
    wherein the first movable wedge includes a proximal planar base surface connected to the adaptor and a distal planar angled surface opposite the proximal planar base surface, wherein the distal planar angled surface is angled relative to the proximal planar base surface such that the first movable wedge has a wedge shaped side profile,
    wherein the second movable wedge includes a distal planar base surface in contact with the fixed base and a proximal planar angled surface opposite the distal planar base surface, wherein the proximal planar angled surface is angled relative to the distal planar base surface such that the second movable wedge has a wedge shaped side profile, and
    wherein the distal planar angled surface of the first movable wedge and the proximal planar angled surface of the second movable surface are in contact and configured to rotate on each other when the first movable wedge and second movable wedge are moved relative to each other.

2. The patient-specific registration jig of claim 1, wherein the patient-specific negative contour is configured to receive a portion of the patient's bony anatomy such that the head is configured to couple to that portion of the patient's bony anatomy in a unique orientation and position relative to the patient's bony anatomy.

3. The patient-specific registration jig of claim 1, wherein the patient-specific registration jig is a patient-specific acetabulum registration jig and the patient-specific contact surface is configured to contact an acetabulum of the patient's bony anatomy.

4. The patient-specific registration jig of claim 3, wherein the patient-specific contact surface includes a patient-specific negative contour configured to receive a portion of the interior bony surface of the acetabulum of the patient's bony anatomy.

5. The patient-specific registration jig of claim 1, wherein the adaptor end includes a first keyed feature configured to mate with a second keyed feature of the clutch of the orthopaedic surgical instrument.

6. The patient-specific registration jig of claim 1, further comprising a tracking sensor configured for interaction with an orthopaedic surgical navigation system to facilitate tracking of a position of the patient-specific registration jig.

7. The patient-specific registration jig of claim 1, wherein each of the first movable wedge and the second movable wedge is movable relative to the fixed base to modify the inclination angle or the version angle of the head relative to the adaptor.

8. The patient-specific registration jig of claim 7, wherein each of the first movable wedge and the second movable wedge is rotatably coupled to the fixed base such that each of the first and second movable wedges is independently rotatably, relative to the fixed base, about an axis of rotation defined by the adaptor.

9. The patient-specific registration jig of claim 7, wherein one of the first movable wedge or the second movable wedge is movable, relative to the fixed base, to adjust the inclination angle of the head relative to the adaptor and the other one of the first movable wedge or the second movable wedge is movable, relative to the fixed base, to adjust the version angle of the head relative to the adaptor.

10. The patient-specific registration jig of claim 1, wherein each of the first movable wedge and the second movable wedge has a cylindrical wedge shape.

* * * * *